United States Patent [19]

Randazzo

[11] Patent Number: 5,948,640
[45] Date of Patent: Sep. 7, 1999

[54] MAMMALIAN ADDITIONAL SEX COMBS (MAMMALIAN ASX) ACTS AS A TUMOR SUPPRESSOR

[75] Inventor: Filippo M. Randazzo, Emeryville, Calif.

[73] Assignee: Chiron Corporation, Emeryville, Calif.

[21] Appl. No.: 08/853,310

[22] Filed: May 8, 1997

Related U.S. Application Data

[60] Provisional application No. 60/016,585, May 8, 1996, and provisional application No. 60/021,383, Jul. 8, 1996.

[51] Int. Cl.$^6$ ............................ C12P 21/06; C12N 15/00; C12N 5/00; C07H 21/02
[52] U.S. Cl. ...................... 435/69.1; 435/455; 435/320.1; 435/325; 536/23.1
[58] Field of Search .......................... 536/23.1; 435/69.1, 435/320.1, 455, 325

[56] References Cited

PUBLICATIONS

Sato et al., "Homoeosis in Drosophilia: A New Enhancer of Polycomb and Related Homoeotic Mutations" *Genetics* *105*: 357–370, Oct., 1983.
Kennison and Tamkun, "Dosage–Dependent Modifiers of Polycomb and Antennapedia Mutations in Drosphila" *Proc. Natl. Acad. Sci. USA* 85: 8136–8140, Nov., 1988.
Lewin, "Commitment and Activation at Pol II Promoters: A Tail of Protein—Protein Interactions" *Cell* 61: 1161–1164, Jun., 1990.
Paro, "Imprinting a Determined State into the Chromatin of Drosophila" *TIG* 6(12): 416–421, Dec., 1990.
Goebl, "The bmi–1 and mel–18 Gene Products Define a New Family of DNA–Binding Proteins Involved in Cell Proliferation and Tumorigenesis" *Cell* 66:623, Aug., 1991.
Brunk et al., "Drosophila Genes Posterior Sex Combs and Suppressor Two of Zeste Encode Proteins With Homology to the Murine bmi–1 Oncogene" *Nature* 353:351–353, Sep., 1991.
van Lohuizen et al., "Sequence Similarity Between the Mammalian bmi–1 Proto–Oncogene and the Drosophila Regulatory Genes Psc and Su(z)2" *Nature* 353:353–355, Sep., 1991.
DeCamillis et al., "The Polyhomeotic Gene of Drosophila Encodes a Chromatin Protein that Shares Polytene Chromosome–Binding Sites with Polycomb" *Genes and Development* 6:223–232, 1992.
Felsenfeld, "Chromatin as an Essential Part of the Transcriptional Mechanism" *Nature* 355:219–224, Jan., 1992.
Sinclair et al., "Genetic Analysis of the Additional Sex Combs Locus of *Drosophila melanogaster*" *Genetics* 130:817–825, Apr., 1992.
Travers, "The Reprogramming of Transcriptional Competence" *Cell* 69:573–575, May, 1992.
Djabali et al., "A Trithorax–Like Gene is Interrupted by Chromosome 11q23 Translocations in Acute Leukaemias" *Nature Genetics* 2:113–118, Oct. 1992.

Gu et al., "The t(4;11) Chromosome Translocation of Human Acute Leukemias Fuses the ALL–1 Gene, Related to *Drosophila trithorax*, to the AF–4 Gene" *Cell* 71:701–708, Nov., 1992.
Tkachuk et al., "Involvement of a Homolog of *Drosophila trithorax* by 11q23 Chromosomal Translocations in Acute Leukemias" *Cell* 71:691–700, Nov., 1992.
Winston and Carlson, "Yeast SNF/SWI Transcriptional Activators and the SPT/SIN Chromatin Connection" *TIG* 8(11):387–391, Nov., 1992.
Barba et al., "Hox Gene Expression in Human Cancers" *Advances in Nutrition and Cancer* pp. 45–57, 1993.
Cillo, "Hox Genes in Human Cancers" *Invasion Metastasis* 14:38–49, 1994–1995.
Moehrle and Paro, "Spreading the Silence: Epigenetic Transcriptional Regulation During Drosophila Development" *Developmental Genetics* 15:478–484, 1994.
Kennison, "Transcriptional Activation of Drosophila Homeotic Genes from Distant Regulatory Elements" *TIG* 9(3):75–79, Mar., 1993.
van deg Lugt et al., "Posterior Transformation, Neurological Abnormalities, and Severe Hematopoietic Defects in Mice with a Targeted Deletion of the bmi–1 proto–oncogene" *Genes and Development* 8:757–769, 1994.
Denis and Green, "A Novel, Mitogen–Activated Nuclear Kinase is Related to a Drosophila Developmental Regulator" *Genes and Development* 10:261–271, 1996.
Epstein, "Polycomb and Friends" *BioEssays*14(6):411–413, 1992.
Chiba et al., "Two Human Homologues of *Saccharomyces cerevisiae* SW12/SNF2 and *Drosophila brahma* are Transcriptional Coactivators Cooperating with the Estrogen Receptor and the Retinoic Acid Receptor" *Nucleic Acids Research* 22(10):1815–1820. 1994.
Nomura et al., "Isolation and Characterization of Retinoic Acid–Inducible cDNA Clones in F9 Cells: One of the Early Inducible Clones Encodes a Novel Protein Sharing Several Highly Homologous Regions with a *Drosophila polyhomeotic* Protein" *Differentiation* 57:39–50, 1994.
Watson et al., "Drosophila in Cancer Research: the First Fifty Tumor Suppressor Genes" *J. Cell Science* 18:19–33, 1994.

(List continued on next page.)

*Primary Examiner*—Paula K. Hutzell
*Assistant Examiner*—Lin Sun-Hoffman
*Attorney, Agent, or Firm*—Seed and Berry LLP

[57] ABSTRACT

Mammalian Asx gene and amino acid sequences encoded by the mammalian Asx gene, are described. The mammalian Asx gene and gene products are useful for diagnostic and therapeutic applications in proliferative and developmental disorders. Modulators of mammalian Asx can be identified using the disclosed genes. The modulators can be used in the context of cancer therapy or a treatment of a developmental disorder. Asx is also useful for inducing differentiation in a population of progenitor cells.

11 Claims, No Drawings

OTHER PUBLICATIONS

Kanno et al., "mel–18, a Polycomb Group–Related Mammalian Gene, Encodes a Transcriptional Negative Regulator With Tumor Suppressive Activity" *The EMBO Journal* 14(22):5672–5678, 1995.

Santamaria and Randsholt, "Characterization of a Region of the X Chromosome of Drosophila Including multi sex combs (mxc), a Polycomb Group Gene which also Functions as a Tumour Suppressor" *Mol. Gen. Genet.* 246:282–290, 1995.

Pirrotta, "Chromatin Complexes Regulating Gene Expression in Drosophila" *Current Opinion in Genetics and Development* 5:466–472, 1995.

Stuart et al., "PAX and HOX in Neoplasia" *Advances in Genetics* 33:255–274, 1995.

Tamkun, "The Role of Brahma and Related Proteins in Transcription and Development" *Current Opinion in Genetics and Development* 5:473–477, 1995.

Yu et al., "Altered Hox Expression and Segmental Identity in MII–mutant Mice" *Nature* 378:505–508, Nov., 1995.

Wallace and Miyada, "Oligonucleotide Probes for the Screening of Recombinant DNA Libraries" *Methods in Enzymology* 152:432–442, 1987.

Cheng et al., "Interactions of *polyhomeotic* With Polycomb Group Genes of *Drosophila melanogaster*" *Genetics* 138:1151–1162, Dec., 1994.

Soto et al., "Comparison of Germline Mosaics of Genes in the Polycomb Group of *Drosophila melanogaster*" *Genetics* 140:231–243, May, 1995.

Kidd, S., et al., *Molecular & Cellular Biology* (1986) 6(9):3094–3108.

Tautz, D., *Nucleic Acids Research* (1989) 17(16):6463–6471.

Adams, M., et al., Nature (1992) 355:632–634.

Matsubara et al. Genbank, accession No. T26123, Oct., 1996.

Hillier et al. Genbank, accession No. R61738, May 1995.

MAMMALIAN ADDITIONAL SEX COMBS (MAMMALIAN ASX) ACTS AS A TUMOR SUPPRESSOR

This application claims the benefit of provisional applications Ser. No. 60/016,585 filed May 8, 1996 and Ser. No. 60/021,383 filed Jul. 8, 1996.

FIELD OF THE INVENTION

The invention relates to a gene, mammalian Additional Sex Combs (mammalian Asx), implicated in proliferative disorders, including malignancies, and in developmental processes.

BACKGROUND OF THE INVENTION

Cancer and malignancy therapies have included treatment with chemical toxins, radiation, and surgery. Genes known to be over-expressed or underexpressed in cancer are used for diagnosis of the disease and evaluation of a patient's progression with the disease and treatment.

The study of transcription has provided information about cell differentiation: early in the development of a cell lineage, transcription factors direct development along a particular pathway by activating genes of a differentiated phenotype. Differentiation can involve not only changes in patterns of expressed genes, but also involve the maintenance of those new patterns.

The genetic basis of mammalian development, and the genetic link between development and cancer has not been fully elucidated. There is a need in the art for knowledge of the key genes underlying mammalian cancer, particularly those also implicated in normal mammalian developmental processes.

SUMMARY OF THE INVENTION

In one embodiment of the invention an isolated mammalian Asx (mammalian Asx) polypeptide is provided. The polypeptide comprises a sequence of at least 18 consecutive amino acids of the sequence of SEQ ID NO: 2.

In another embodiment of the invention an isolated nucleic acid molecule is provided. The nucleic acid molecule encodes a polypeptide having the sequence of SEQ ID NO: 2.

According to yet another embodiment, an isolated nucleic acid molecule is provided which comprises at least 13 contiguous nucleotides selected from the sequence of SEQ ID NO: 1.

In another embodiment of the invention, an antibody preparation is provided. The antibodies specifically bind to an mammalian Asx polypeptide, and do not bind specifically to other mammalian proteins.

In still another embodiment, a method of treating a neoplasm is provided. The method comprises:
contacting a neoplasm with an effective amount of a therapeutic agent comprising a mammalian Asx polypeptide which comprises the sequence of SEQ ID NO:2, whereby growth of the neoplasm is arrested.

In still another embodiment of the invention a method of inducing cell differentiation is provided. The method comprises:
contacting a progenitor cell with a human Asx (hAsx) polypeptide which comprises the sequence of SEQ ID NO: 2, whereby differentiation of the cell is induced.

According to yet another embodiment of the invention a method of regulating cell growth is provided. The method comprises:
contacting a cell whose growth is uncontrolled with a human Asx (hAsx) polypeptide which comprises the sequence of SEQ ID NO: 2, whereby growth of the cell is regulated.

According to yet another aspect of the invention a pharmaceutical composition is provided. The composition comprises an effective amount of a therapeutic agent comprising a mammalian Asx polypeptide which comprises the sequence of SEQ ID NO: 2, and a pharmaceutically acceptable carrier.

Another aspect of the invention is a method of diagnosing neoplasia. The method comprises:
contacting (a) a tissue sample suspected of neoplasia isolated from a patient with (b) an mammalian Asx gene probe comprising at least 13 nucleotides of the sequence of SEQ ID NO: 1, wherein a tissue which underexpresses mammalian Asx or expresses a variant mammalian Asx is categorized as neoplastic.

According to another embodiment of the invention a method of diagnosing neoplasia is provided. The method comprises:
contacting PCR primers which specifically hybridize with an mammalian Asx gene sequence of SEQ ID NO: 1, with nucleic acids isolated from a tissue suspected of neoplasia;
amplifying mammalian Asx sequences in the nucleic acids of the tissue; and
detecting a mutation in the amplified sequence, wherein a mutation is identified when the amplified sequence differs from a sequence similarly amplified from a normal human tissue.

In yet another embodiment of the invention a method of diagnosing neoplasia is provided. The method comprises:
contacting a bDNA probe with nucleic acids isolated from a tissue suspected of neoplasia, wherein the bDNA probe specifically hybridizes with a mammalian Asx gene sequence of SEQ ID NO: 1;
detecting hybrids formed between the bDNA probe and nucleic acids isolated from the tissue; and
identifying a mutation in the nucleic acids isolated from the tissue by comparing the hybrids formed with hybrids similarly formed using nucleic acids from a normal human tissue.

According to still another aspect of the invention a method of diagnosing neoplasia is provided. The method comprises:
contacting a tissue sample suspected of being neoplastic with an antibody selected from the group consisting of: one which specifically binds to wild-type mammalian Asx as shown in SEQ ID NO:2, or one which specifically binds to an expressed mammalian Asx variant;
detecting binding of the antibody to components of the tissue sample, wherein a difference in the binding of the antibody to components of the tissue sample, as compared to binding of the antibody to a normal human tissue sample indicates neoplasia of the tissue.

Another aspect of the invention is yet another method of diagnosing neoplasia. The method comprises:
contacting RNA from a tissue suspected of being neoplastic with PCR primers which specifically hybridize to an mammalian Asx gene sequence as shown in SEQ ID NO: 1 or a bDNA probe which specifically hybridizes to said sequence;
determining quantitative levels of mammalian Asx RNA in the tissue by PCR amplification or bDNA probe detection, wherein lower levels of mammalian Asx RNA as compared to a normal human tissue indicate neoplasia.

Also provided are nucleic acid molecules which can be used in regulating a heterologous coding sequence coordinately with hAsx. These sequences include the 5' untranslated region of an hAsx gene, the 3' untranslated region of an hAsx gene, the promoter region of an hAsx gene, and an intron of an hAsx gene.

Also provided by the present invention is a method of identifying modulators of hAsx function comprising:

contacting a test substance with a human cell which comprises an hAsx gene or a reporter construct comprising an hAsx promoter and a reporter gene;

quantitating transcription of hAsx or the reporter gene in the presence and absence of the test substance, wherein a test substance which increases transcription is a candidate drug for anti-neoplastic therapy.

According to another embodiment a method of diagnosis of neoplasia is provided. The method comprises:

contacting a tissue sample suspected of neoplasia isolated from a patient with an mammalian Asx gene probe comprising at least 13 contiguous nucleotides of the sequence of SEQ ID NO: 1, wherein a tissue which overexpresses mammalian Asx or expresses a variant mammalian Asx is categorized as neoplastic.

In still another aspect of the invention a method of dysregulating cell growth is provided. The method comprises:

contacting a cell whose growth is controlled with a mammalian Asx polypeptide which comprises the sequence of SEQ ID NO: 2, whereby growth of the cell is dysregulated.

According to still another aspect of the invention a method of diagnosing neoplasia is provided. The method comprises:

contacting RNA from a tissue suspected of being neoplastic with PCR primers which specifically hybridize to an mammalian Asx gene sequence as shown in SEQ ID NO: 1, or a bDNA probe which specifically hybridizes to said sequence;

determining quantitative levels of mammalian Asx RNA in the tissue by PCR amplification or bDNA probe detection, wherein higher levels of mammalian Asx RNA as compared to a normal human tissue indicates neoplasia.

Also provided are nucleic acid molecules which can be used in regulating a heterologous coding sequence coordinately with mammalian Asx. These sequences include the 5' untranslated region of an mammalian Asx gene, the 3' untranslated region of an mammalian Asx gene, the promoter region of an mammalian Asx gene, and an intron of an mammalian Asx gene.

Also provided by the present invention is a method of identifying modulators of mammalian Asx function comprising:

contacting a mammalian cell which comprises an mammalian Asx gene or a reporter construct comprising an mammalian Asx promoter and a reporter gene with a test substance;

quantitating transcription of mammalian Asx or the reporter gene in the presence and absence of the test substance, wherein a test substance which decreases transcription is a candidate drug for anti-neoplastic therapy.

DETAILED DESCRIPTION

The inventors have discovered a gene, the mammalian Additional Sex Combs (mammalian Asx), that operates to regulate protein expression in mammals, particularly humans. Mammalian Asx may operate by controlling homeotic gene expression. Although the invention is not limited by any theory or mechanism of how the invention works, it is believed that control by this gene involves multiprotein complexes capable of negative regulation of transcription.

The polypeptides of the invention according to SEQ ID NO: 2 and 4 contain various domains of the mammalian Asx gene. The nucleic acid molecules according to SEQ ID NO: 1 and 3 encode the mammalian Asx polypeptides and have been cloned from mammalian cells. The polynucleotide of SEQ ID NO: 1 encodes the polypeptide of SEQ ID NO: 2; the polynucleotide of SEQ ID NO: 3 encodes the polypeptide of SEQ ID NO: 4. Polypeptides comprising at least 6, 10, 18, 20, 30, 40, 50, 54, 60, 65, or 75 amino acids of mammalian Asx are useful as immunogens for raising antibodies and as competitors in immunoassays. They can also be used to purify antibodies. Nucleic acid molecules of at least 12, 13, 15, 20, 30, 40, or 50 contiguous nucleotides are useful as probes for use in diagnostic assays.

Both human and murine Asx, and their coding sequences, are provided herein. There is sequence conservation between murine and human Asx. They are 84% similar and 75% identical at the amino acid level. Other mammalian Asx proteins and genes can be obtained by screening of cDNA libraries of a mammalian species with a probe derived from the murine or human sequences. Similar levels of identity and similarity are expected with other mammals. Such techniques are well known in the art, and can be employed by those of skill in the art.

The domains of mammalian Asx protein which appear to be most conserved are those found in the following locations in the human protein. The conserved domains are at aa 250–356 and aa 1501–1536. In addition there is a lysine rich putative nuclear translocation sequence from amino acid 2 to 11.

The human Asx gene has been mapped to chromosome 20q11. This was accomplished by FISH mapping. Intriguingly, there are many chromosomal aberrations associated with a variety of cancers which also map to this chromosomal segment.

Mammalian Asx is implicated in development, by contributing to the activation or repression of certain genes during development. Thus mammalian Asx can be used therapeutically to change the gene expression pattern and thus the phenotype of a cell. Thus, for example, mammalian Asx can be used to direct differentiation of a progenitor cell. Similarly, inhibition of mammalian Asx will direct a differentiated cell to become less differentiated, i.e., to alter its pattern of gene expression.

Proliferative indications for which an mammalian Asx-based therapeutic agent can be used include, restinosis, benign prostatic hyperplasia, uterine fibroids, retinopathy, psoriasis, keloids, arthritis, wound healing, and premalignant lesions including for example, intestinal polyps, cervical dysplasia, and myeloid dysplasia. Neoplasias that may be treatable with an mammalian Asx-based therapeutic agent, include, but are not limited to, carcinoma, colorectal adenocarcinoma, leukemia, Burkitt's lymphoma and melanoma.

The coding region of mammalian Asx can be used for expression of mammalian Asx and for development of mammalian Asx variants for therapeutic applications. Mammalian Asx coding sequence can be used as a probe for diagnosis of disease or biological disorder where overexpression of mammalian Asx occurs, such as, for example, in cancers such as carcinoma, colorectal adenocarcinoma, lymphatic cancer, promyelocytic leukemia, Burkitt's lymphoma, melanoma, and myeloma. The 5' untranslated and 3' untranslated regions of mammalian Asx can also be used diagnostically to the same effect as the mammalian Asx coding sequence, for example, the 5' untranslated region can be isolated and used to probe tissue, for example, colon tissue, where colon carcinoma is suspected. Because mammalian Asx has been shown to be upregulated in colon carcinoma, probing with any portion of the mammalian Asx gene can identify the upregulation of mammalian Asx in the tissue, as an aid to making a diagnosis. Such diagnostic probes may also be used for continued monitoring of a diagnosed patient, for signs of improvement after and during treatment, and for indications of progression of the disease.

Mammalian Asx genes can be cloned and isolated by probing genomic DNA with the coding region of mammalian Asx, or by probing genomic DNA with any probe-length piece (at least 13 nucleotides) of mammalian Asx DNA. A P1 clone of genomic DNA containing hAsx (ATCC #98426, CMCC #4738) has been deposited at the American Type Culture Collection, Rockville, Md. The genomic DNA can be subcloned into a cloning vector, for example a cosmid vector, for sequencing and assembly of the entire gene sequence. The promoter region of mammalian Asx is useful for expression of mammalian Asx in a gene therapy protocol, and for further analysis of mammalian Asx gene function and regulatory control. Knowledge of promoter region sequences specific for binding transcriptional activators that activate the mammalian Asx promoter can facilitate improved expression of mammalian Asx for therapeutic purposes. The mammalian Asx promoter region may be useful for tissue specific expression of heterologous genes, such as, for treatment of colon cancer. The region immediately 5' of the coding region of mammalian Asx can be used, for example, as a diagnostic probe for cancer or a developmental disorder associated with aberrant mammalian Asx activity. The full length gene, or such non-coding regions of it as the promoter and the 5' or 3' untranslated regions can be isolated by probing genomic DNA with a probe comprising at least about 13 nucleotides of mammalian Asx cDNA, and retrieving a genomic sequence that hybridizes to one of these sequences. The 5' untranslated end and the promoter regions, for example, can be cloned by PCR cloning with random oligonucleotide and a 5' portion of the known coding sequence.

The polypeptides of the invention can further be used to generate monoclonal or polyclonal antibodies. Monoclonal antibodies, are prepared using the method of Kohler and Milstein, as described in *Nature* (1975) 256: 495–96, or a modification thereof. Antibodies to mammalian Asx or fragments or fusion proteins thereof, either polyclonal or monoclonal, can be used therapeutically. They are desirably compatible with the host to be treated. For example, for treatment of humans, the antibodies can be human monoclonal antibodies or humanized antibodies, as the term is generally known in the art. Alternatively, single chain antibodies may be used for therapy. Antibodies may act to antagonize or inhibit the polypeptide activity of mammalian Asx, and are also useful in diagnosing a condition characterized by mammalian Asx expression or over-expression, such as, for example, a malignancy condition. Similarly, over- or under-expression can be detected using such antibodies bind specifically to mammalian Asx but not to other human proteins. More preferred is the situation where the antibodies are human species mammalian Asx-specific.

Expression of mammalian Asx can be accomplished by any expression system appropriate for the purpose and conditions presented. Some exemplary expression systems are listed below. Where mammalian Asx itself is used as a therapeutic, the polypeptide can be expressed and subsequently administered to a patient. Alternatively a gene encoding at least a functional portion of mammalian Asx can be administered to a patient for expression in the patient.

Recombinant mammalian Asx may be used as a reagent for diagnostic methods or diagnosis of cancer or a developmental disorder. It may also be used as a therapeutic for inducing differentiation in a population of progenitor cells. Recombinant mammalian Asx can also be used to develop modulators of mammalian Asx for achieving a desired therapeutic effect. Construction and expression of any of the recombinant molecules of the invention can be accomplished by any expression system most appropriate for the task, including, for example, an expression system described below.

Expression Systems

Although the methodology described below is believed to contain sufficient details to enable one skilled in the art to practice the present invention, other constructs can be constructed and purified using standard recombinant DNA techniques as described in, for example, Sambrook et al. (1989), MOLECULAR CLONING: A LABORATORY MANUAL, 2nd ed. (Cold Spring Harbor Press, Cold Spring Harbor, N.Y.); and under current regulations described in United States Dept. of Health and Human Services, National Institutes of Health (NIH) Guidelines for Recombinant DNA Research. The polypeptides of the invention can be expressed in any expression system, including, for example, bacterial, yeast, insect, amphibian and mammalian systems. Expression systems in bacteria include those described in Chang et al., *Nature* (1978) 275: 615, Goeddel et al., *Nature* (1979) 281: 544, Goeddel et al., *Nucleic Acids Res.* (1980) 8: 4057, EP 36,776, U.S. Pat. No. 4,551,433, deBoer et al., *Proc. Natl. Acad. Sci. U.S.A.* (1983) 80: 21–25, and Siebenlist et al., *Cell* (1980) 20: 269. Expression systems in yeast include those described in Hinnen et al., *Proc. Natl. Acad. Sci. U.S.A.* (1978) 75: 1929; Ito et al., *J. Bacteriol.* (1983) 153: 163; Kurtz et al., *Mol. Cell. Biol.* (1986) 6: 142; Kunze et al., *J. Basic Microbiol.* (1985) 25: 141; Gleeson et al., *J. Gen. Microbiol.* (1986) 132: 3459, Roggenkamp et al., *Mol. Gen. Genet.* (1986) 202: 302) Das et al., *J. Bacteriol.* (1984) 158: 1165; De Louvencourt et al., *J. Bacteriol.* (1983) 154: 737, Van den Berg et al., *Bio/Technology* (1990) 8: 135; Kunze et al., *J. Basic Microbiol.* (1985) 25: 141; Cregg et al., *Mol. Cell. Biol.* (1985) 5: 3376, U.S. Pat. No. 4,837,148, U.S. Pat. No. 4,929,555; Beach and Nurse, *Nature* (1981) 300: 706; Davidow et al., *Curr. Genet.* (1985) 10: 380, Gaillardin et al., *Curr. Genet.* (1985) 10: 49, Ballance et al., *Biochem. Biophys. Res. Commun.* (1983) 112: 284–289; Tilburn et al., *Gene* (1983) 26: 205–221, Yelton et al., *Proc. Natl. Acad. Sci. U.S.A.* (1984) 81: 1470–1474, Kelly and Hynes, *EMBO J.* (1985) 4: 475479; EP 244,234, and WO 91/00357. Expression of heterologous genes in insects can be accomplished as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol.* (1988) 69: 765–776, Miller et al., *Ann. Rev. Microbiol.* (1988) 42: 177, Carbonell et al., *Gene* (1988) 73: 409, Maeda et al., *Nature* (1985) 315: 592–594, Lebacq-Verheyden et al., *Mol. Cell. Biol.* (1988) 8: 3129; Smith et al., *Proc. Natl. Acad. Sci. U.S.A.* (1985) 82: 8404, Miyajima et al., *Gene* (1987) 58: 273; and Martin et al., *DNA* (1988) 7:99. Numerous baculoviral strains and variants and corresponding permissive insect host cells from hosts are described in Luckow et al., *Bio/Technology* (1988) 6: 47–55, Miller et al., in GENERIC ENGINEERING (Setlow, J. K. et al. eds.), Vol. 8 (Plenum Publishing, 1986), pp. 277–279, and Maeda et al., *Nature,* (1985) 315: 592–594. Mammalian expression can be accomplished as described in Dijkema et al., *EMBO J.* (1985) 4: 761, Gorman et al., *Proc. Natl. Acad. Sci. U.S.A.* (1982b) 79: 6777, Boshart et al., *Cell* (1985) 41: 521 and U.S. Pat. No. 4,399,216. Other features of mammalian expression can be facilitated as described in Ham and Wallace, *Meth. Enz.* (1979) 58: 44, Barnes and Sato, *Anal. Biochem.* (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. Pat. No. Re. 30,985.

Constructs including mammalian Asx coding sequence or constructs including coding sequences for modulators of mammalian Asx can be administered by a gene therapy protocol, either locally or systemically. These constructs can utilize viral or non-viral vectors and can be delivered in vivo or ex vivo or in vitro. Expression of such coding sequence can be driven by endogenous mammalian or heterologous promoters. Expression of the coding sequence in vivo can be either constitutive or regulated.

Gene delivery vehicles (GDVs) are available for delivery of polynucleotides to cells, tissue, or to a the mammal for expression. For example, a polynucleotide sequence of the invention can be administered either locally or systemically in a GDV. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated. The invention includes gene delivery vehicles capable of expressing the contemplated polynucleotides. The gene delivery vehicle is preferably a viral vector and, more preferably, a retroviral, adenovirmal, adeno-associated viral (AAV), herpes viral, or alphavirus vectors. The viral vector can also be an astrovirus, coronavirus, orthomyxovirus, papovavirus, paramyxovirus, parvovirus, picornavirus, poxvirus, togavirus viral vector. See generally, Jolly, Cancer Gene Therapy 1:51–64 (1994); Kimura, Human Gene Therapy 5:845–852 (1994), Connelly, Human Gene Therapy 6:185–193 (1995), and Kaplitt, Nature Genetics 6:148–153 (1994). Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill, J. Vir. 53:160, 1985) polytropic retroviruses (for example, MCF and MCF-MLV (see Kelly, J. Vir. 45:291, 1983), spumaviruses and lentiviruses. See RNA Tumor Viruses, Second Edition, Cold Spring Harbor Laboratory, 1985.

Portions of the retroviral gene therapy vector may be derived from different retroviruses. For example, retroviral LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus. These recombinant retroviral vectors may be used to generate transduction competent retroviral vector particles by introducing them into appropriate packaging cell lines (see U.S. Ser. No. 07/800,921, filed Nov. 29, 1991). Retrovirus vectors can be constructed for site-specific integration into host cell DNA by incorporation of a chimeric integrase enzyme into the retroviral particle. See, U.S. Ser. No. 08/445,466 filed May 22, 1995. It is preferable that the recombinant viral vector is a replication defective recombinant virus. Packaging cell lines suitable for use with the above-described retrovirus vectors are well known in the art, are readily prepared (see U.S. Ser. No. 08/240,030, filed May 9, 1994; see also WO 92/05266), and can be used to create producer cell lines (also termed vector cell lines or "VCLs") for the production of recombinant vector particles. Preferably, the packaging cell lines are made from human parent cells (e.g., HT1080 cells) or mink parent cell lines, which eliminates inactivation in human serum. Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe, J. Virol. 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques. Exemplary known retroviral gene therapy vectors employable in this invention include those described in GB 2200651; EP No. 415,731; EP No. 345,242; PCT Publication Nos. WO 89/02468, WO 89/05349, WO 89/09271, WO 90/02806, WO 90/07936, WO 90/07936, WO 94/03622, WO 93/25698, WO 93/25234, WO 93/11230, WO 93/10218, and WO 91/02805, in U.S. Pat. Nos. 5,219,740, 4,405,712, 4,861,719, 4,980, 289 and 4,777,127, in U.S. Ser. No. 07/800,921 and in Vile, Cancer Res. 53:3860–3864 (1993); Vile, Cancer Res 53:962–967 (1993); Ram, Cancer Res 53:83–88 (1993); Takamiya, J. Neurosci. Res. 33:493–503 (1992); Baba, J Neurosurg 79:729–735 (1993); Mann, Cell 33:153 (1983); Cane, Proc Natl Acad Sci 81:6349 (1984) and Miller, Human Gene Therapy 1 (1990). Human adenoviral gene therapy vectors are also known in the art and employable in this invention. See, for example, Berkner, Biotechniques 6:616 (1988), and Rosenfeld, Science 252:431 (1991), and PCT Patent Publication Nos. WO 93/07283, WO 93/06223, and WO 93/07282. Exemplary known adenoviral gene therapy vectors employable in this invention include those described in the above-referenced documents and in PCT Patent Publication Nos. WO 94/12649, WO 93/03769, WO 93/19191, WO 94/28938, WO 95/11984, WO 95/00655, WO 95/27071, WO 95/29993, WO 95/34671, WO 96/05320, WO 94/08026, WO 94/11506, WO 93/06223, WO 94/24299, WO 95/14102, WO 95/24297, WO 95/02697, WO 94/28152, WO 94/24299, WO 95/09241, WO 95/25807, WO 95/05835, WO 94/18922 and WO 95/09654. Alternatively, administration of DNA linked to killed adenovirus as described in Curiel, Hum. Gene Ther. 3:147–154 (1992) may be employed. The gene delivery vehicles of the invention also include adenovirus asssociated virus (AAV) vectors. Leading and preferred examples of such vectors for use in this invention are the AAV-2 basal vectors disclosed in Srivastava, PCT Patent Publication No. WO 93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini, Gene 124:257–262 (1993). Another example of such an AAV vector is psub201. See Samulski, J. Virol. 61:3096 (1987). Another exemplary AAV vector is the Double-D ITR vector. How to make the Double D ITR vector is disclosed in U.S. Pat. No. 5,478,745. Still other vectors are those disclosed in Carter, U.S. Pat. No. 4,797,368 and Muzyczka, U.S. Pat. No. 5,139,941, Chartejee, U.S. Pat. No. 5,474,935, and Kotin, PCT Patent Publication No. WO 94/288157. Yet a further example of an AAV vector employable in this invention is SSV9AFABTKneo, which contains the AFP enhance and albumin promoter and directs expression predominantly in the liver. Its structure and how to make it are disclosed in Su,Human Gene Therapy 7:463–470 (1996). Additional AAV gene therapy vectors are described in U.S. Pat. Nos. 5,354,678; 5,173,414; 5,139,941; and 5,252,479. The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP No. 176,170 (Roizman). Additional exemplary herpes simplex virus vectors include HFEM/ICP6-LacZ disclosed in PCT Patent No. WO 95/04139 (Wistar Institute), pHSVlac described in Geller, Science 241:1667–1669 (1988) and in PCT Patent Publication Nos. WO 90/09441 and WO 92/07945, HSV Us3::pgC-lacZ described in Fink, Human Gene Therapy 3:11–19 (1992) and HSV 7134, 2 RH 105 and GAL4 described in EP No. 453,242 (Breakefield), and those deposited with the ATCC as accession numbers ATCC VR-977 and ATCC VR-260. Alpha virus gene therapy vectors may be employed in this invention. Preferred alpha virus vectors are Sindbis viruses vectors. Togaviruses, Semliki Forest virus (ATCC VR67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described U.S. Pat. Nos. 5,091,309 and 5,217,879, and PCT Patent Publication No. WO 92/10578. More particularly, those alpha virus vectors described in U.S. Ser. No. 08/405, 627, filed Mar. 15, 1995, and U.S. Ser. No. 08/198,450 and in PCT Patent Publication Nos. WO 94/21792, WO 92/10578, and WO 95/07994, and U.S. Pat. Nos. 5,091,309 and 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see co-owned U.S. Ser. No. 08/679640). DNA vector systems such as eukaryotic layered expression systems are also useful for expressing the nucleic acids of the invention. See PCT Patent Publication No. WO 95/07994 for a detailed description of eucaryotic layered expression systems. Preferably, the eukaryotic layered expression systems of the invention are derived from alphavirus vectors and most preferably from Sindbis viral vectors. Other viral vectors suitable for use in the present invention include those derived from poliovirus, for example ATCC VR-58 and those described in Evans, Nature 339:385 (1989), and Sabin, J. Biol. Standardization 1:115 (1973); rhinovirus, for example ATCC VR-1110 and those described in Arnold, J Cell Biochem (1990) L401; pox viruses such as canary pox virus or vaccinia virus, for example ATCC VR-111 and ATCC VR-2010 and those described in Fisher-Hoch, Proc Natl Acad Sci 86 (1989) 317, Flexner, Ann NY Acad Sci 569:86 (1989), Flexner, Vaccine 8:17 (1990); in U.S. Pat. Nos. 4,603,112 and 4,769,330 and in WO 89/01973; SV40 virus, for example ATCC VR-305 and those described in Mulligan, Nature 277:108 (1979) and Madzak, J Gen Vir 73:1533 (1992); influenza virus, for example ATCC VR-797 and recombinant influenza viruses made employing reverse genetics techniques as described in U.S. Pat. No. 5,166,057 and in Enami, Proc. Natl. Acad. Sci. 87:3802–3805 (1990); Enami and Palese, J. Virol. 65:2711–2713 (1991); and Luytjes, Cell 59:110 (1989), (see also McMicheal., New England J. Med. 309:13 (1983), and Yap, Nature 273:238 (1978) and Nature 277:108, 1979); human immunodeficiency virus as described in EP No. 386,882 and in Buchschacher, J. Vir. 66:2731 (1992); measles virus, for example, ATCC VR-67 and VR-1247 and those described in EP No. 440,219; Aura virus, for example, ATCC VR-368; Bebaru virus, for example, ATCC VR600 and ATCC VR-1240; Cabassou virus, for example, ATCC VR-922; Chikungunya virus, for example, ATCC VR-64 and ATCC VR-1241; Fort Morgan Virus, for example, ATCC VR-924; Getah virus, for example, ATCC VR-369 and ATCC VR-1243; Kyzylagach virus, for example, ATCC VR-927; Mayaro virus, for example, ATCC VR-66; Mucambo virus, for example, ATCC VR-580 and ATCC VR-1244; Ndumu virus, for example, ATCC VR-371; Pixuna virus, for example, ATCC VR-372 and ATCC VR-1245; Tonate virus, for example, ATCC VR-925; Triniti virus, for example ATCC VR469; Una virus, for example, ATCC VR-374; Whataroa virus, for example ATCC VR-926; Y-62-33 virus, for example, ATCC VR-375; O'Nyong virus, Eastern encephalitis virus, for example, ATCC VR-65 and ATCC VR-1242; Western encephalitis virus, for example, ATCC VR-70, ATCC VR-1251, ATCC VR-622 and ATCC VR-1252; and coronavirus, for example, ATCC VR-740 and those described in Hamre, Proc. Soc. Exp. Biol. Med. 121:190(1966). Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994, and Curiel, Hum Gene Ther 3:147–154 (1992) ligand linked DNA, for example, see Wu, J. Biol. Chem. 264:16985–16987 (1989), eukaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in PCT Patent Publication No. WO 92/11033, nucleic charge neutralization or fusion with cell membranes. Additional approaches are described in Philip, Mol. Cell. Biol. 14:2411–2418 (1994) and in Woffendin, Proc. Natl. Acad. Sci. 91:1581–585 (1994). Particle mediated gene transfer may be employed, for example see U.S. provisional application No. 60/023,867. Briefly, the sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, as described in Wu and Wu, J. Biol. Chem. 262:4429–4432 (1987), insulin as described in Hucked, Biochem. Pharmacol. 40:253–263 (1990), galactose as described in Plank, Bioconjugate Chem 3:533–539 (1992), lactose or transferrin. Naked DNA may also be employed. Exemplary naked DNA introduction methods are described in PCT Patent Publication No. WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Patent Publication Nos. WO 95/13796, WO 94/23697, and WO 91/144445, and EP No. 524,968. As described in co-owned U.S. provisional application No. 60/023,867, on non-viral delivery, the nucleic acid sequences can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al., Proc. Natl. Acad. Sci. U.S.A. 91(24):11581–11585 (1994). Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT Patent Publication No. WO 92/11033. Exemplary liposome and polycationic gene delivery vehicles are those described in U.S. Pat. Nos. 5,422,120 and 4,762,915, in PCT Patent Publication Nos. WO 95/13796, WO 94/23697, and WO 91/14445, in EP No. 524,968 and in Stryer, Biochemistry, pages 236–240 (1975) W. H. Freeman, San Francisco, Szoka, Biochem. Biophys. Acta. 600:1 (1980); Bayer, Biochem. Biophys. Acta. 550:464 (1979); Rivnay, Meth. Enzymol. 149:119 (1987); Wang, Proc. Natl. Acad. Sci. 84:7851 (1987); and Plant, Anal. Biochem. 176:420 (1989).

Test compounds can be tested as candidate modulators by testing the ability to increase or decrease the expression of mammalian Asx. The candidate modulators can be derived from any of the various possible sources of candidates, such as for example, libraries of peptides, peptoids, small molecules, polypeptides, antibodies, polynucleotides, small molecules, antisense molecules, ribozymes, cRNA, cDNA, polypeptides presented by phage display. Described below are some exemplary and possible sources of candidates, including synthesized libraries of peptides, peptoids, and small molecules. The exemplary expression systems can be used to generate cRNA or cDNA libraries that can also be screened for the ability to modulate mammalian Asx activity or expression. Candidate molecules screened for the ability to agonize mammalian Asx expression or activity may be useful for inducing differentiation in a population of progenitor cells. Small molecules can be screened for the ability to either affect mammalian Asx expression or affect mammalian Asx function by enhancing or interfering in mammalian Asx's ability to interact with other molecules that mammalian Asx normally interacts with in mammalian Asx's normal function.

Mammalian Asx peptide modulators are screened using any available method. The assay conditions ideally should resemble the conditions under which the mammalian Asx modulation is exhibited in vivo, that is, under physiologic pH, temperature, ionic strength, etc. Suitable antagonists will exhibit strong inhibition of mammalian Asx expression or activity at concentrations that do not cause toxic side effects in the subject. A further alternative agent that can be used herein as a modulator of mammalian Asx is a small molecule antagonist. Small molecules can be designed and screened from a pool of synthetic candidates for ability to modulate mammalian Asx. There exist a wide variety of small molecules, including peptide analogs and derivatives, that can act as inhibitors of proteins and polypeptides. Libraries of these molecules can be screened for those compounds that inhibit the activity or expression of mammalian Asx. Similarly, ribozymes can be screened in assays appropriate for ribozymes, taking into account the special biological or biochemical nature of ribozymes. Assays for affecting mammalian Asx expression can measure mammalian Arc message or protein directly, or can measure a reporter gene expression which is under the control of an mammalian Asx promoter and/or 5' untranslated region (UTR).

Mammalian Asx or a modulator of mammalian Asx can be administered to a patient exhibiting a condition characterized by abnormal cell proliferation, in which aberrant mammalian Asx gene expression is implicated, particularly excessive mammalian Asx activity, or excessive activity controlled or induced by mammalian Asx activity. The modulator can be incorporated into a pharmaceutical composition that includes a pharmaceutically acceptable carrier for the modulator. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared.

Liposomes are included within the definition of a pharmaceutically acceptable carrier. The term "liposomes" refers to, for example, the liposome compositions described in U.S. Pat. No. 5,422,120, WO 95/13796, WO 94/23697, WO 91/14445 and EP 524,968 B1. Liposomes may be pharmaceutical carriers for the peptides, polypeptides or polynucleotides of the invention, or for combination of these therapeutics.

Any therapeutic of the invention, including, for example, polynucleotides for expression in the patient, or ribozymes or antisense oligonucleotide, can be formulated into an enteric coated tablet or gel capsule according to known methods in the art. These are described in the following patents: U.S. Pat. No. 4,853,230, EP 225,189, AU 9,224, 296, AU 9,230,801, and WO 92144,52. Such a capsule is administered orally to be targeted to the jejunum. At 1 to 4 days following oral administration expression of the polypeptide, or inhibition of expression by, for example a ribozyme or an antisense oligonucleotide, is measured in the plasma and blood, for example by antibodies to the expressed or non-expressed proteins.

Administration of a therapeutic agent of the invention, including for example an mammalian Asx modulator, includes administering a therapeutically effective dose of the therapeutic agent by a means considered or empirically deduced to be effective for inducing the desired effect in the patient. Both the dose and the administration means can be determined based on the specific qualities of the therapeutic, the condition of the patient, the progression of the disease, and other relevant factors. Administration of the therapeutic agents of the invention can include, local or systemic administration, including injection, oral administration, particle gun or catheterized administration, and topical administration. The therapeutics of the invention can be administered in a therapeutically effective dosage and amount, in the process of a therapeutically effective protocol for treatment of the patient. The initial and any subsequent dosages administered will depend upon the patient's age, weight, condition, and the disease, disorder or biological condition being treated. Depending on the therapeutic, the dosage and protocol for administration will vary, and the dosage will also depend on the method of administration selected, for example, local or systemic administration.

For polypeptide therapeutics, for example, a dominant negative mammalian Asx polypeptide or a polypeptide modulator of mammalian Asx, the dosage can be in the range of about 5 µg to about 50 µg/kg of patient body weight, also about 50 µg to about 5 mg/kg, also about 100 µg to about 500 µg/kg of patient body weight, and about 200 to about 250 µg/kg.

For polynucleotide therapeutics, depending on the expression of the polynucleotide in the patient, for tissue targeted administration, vectors containing expressible constructs including mammalian Asx coding sequences or modulator coding sequences, or non-coding sequences can be administered in a range of about 100 ng to about 200 mg of DNA for local administration in a gene therapy protocol, also about 500 ng to about 50 mg, also about 1 ug to about 2 mg of DNA, about 5 ug of DNA to about 500 ug of DNA, and about 20 ug to about 100 ug during a local administration in a gene therapy protocol, and for example, a dosage of about 500 ug, per injection or administration.

Non-coding sequences that act by a catalytic mechanism, for example, catalytically active ribozymes may require lower doses than non-coding sequences that are held to the restrictions of stoichiometry, as in the case of, for example, antisense molecules, although expression limitations of the ribozymes may again raise the dosage requirements of ribozymes being expressed in vivo in order that they achieve efficacy in the patient. Factors such as method of action and efficacy of transformation and expression are therefore considerations that will effect the dosage required for ultimate efficacy for DNA and nucleic acids. Where greater expression is desired, over a larger area of tissue, larger amounts of DNA or the same amounts readministered in a successive protocol of administrations, or several administrations to different adjacent or close tissue portions of for example, a tumor site, may be required to effect a positive therapeutic outcome.

For administration of small molecule modulators of mammalian Asx polypeptide activity, depending on the potency of the small molecule, the dosage may vary. For a very potent inhibitor, microgram (µg) amounts per kilogram of patient may be sufficient, for example, in the range of about 1 µg/kg to about 500 mg/kg of patient weight, and about 100 µg/kg to about 5 mg/kg, and about 1 µg/kg to about 50 µg/kg, and, for example, about 10 ug/kg. For administration of peptides and peptoids the potency also affects the dosage, and may be in the range of about 1 µg/kg to about 500 mg/kg of patient weight, and about 100 µg/kg to about 5 mg/kg, and about 1 µg/kg to about 50 µg/kg, and a usual dose might be about 10 ug/kg.

In all cases, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations.

Diagnostic assays for Asx sequence can be applied to cancers demonstrating upregulation of Asx transcript, particularly to cancers of lymphoma, myeloma, and adenocarcinoma. Such diagnostics can be accomplished using any portion of the Asx gene, including the 3' and 5' untranslated regions of the gene, to probe patient tissues to determine an upregulation of an Asx transcript.

Administration of a therapeutic agent for a condition in which increased expression of mammalian Asx is implicated, for example, in the case of promyelocytic leukemia, chronic myelogenous leukemia, lymphoblastic leukemia, Burkitt's lymphoma, colorectal adenocarcinoma, melanoma, and lymphoma, can be preceded by diagnosis of the condition using an mammalian Asx probe, generated from any portion of the mammalian Asx gene, and probing the suspect tissue. bDNA technology using bDNA probes to mammalian Asx gene sequences or mammalian Asx mRNA sequences may be used, as described in WO 92/02526 or U.S. Pat. No. 5,451,503, and U.S. Pat. No. 4,775,619.

Once diagnosis is complete, treatment can include administration of mammalian Asx polynucleotides or anti-sense oligonucleotide by a gene therapy protocol, or by administration by other means including local or systemic administration, of an mammalian Asx modulator, for example an mammalian Asx-specific ribozyme, or a genetically altered mammalian Asx variant, for example a dominant negative mammalian Asx, or a small molecule or peptide or peptoid mammalian Asx modulator, or any combination of these potential therapeutics. The patient can be subsequently monitored by periodic reprobing of the affected tissue with an mammalian Asx probe.

Even in cancers where mammalian Asx mutations are not implicated, mammalian Asx upregulation or enhancement of mammalian Asx function may have therapeutic application. In these cancers, increasing mammalian Asx expression or enhancing mammalian Asx function may help to suppress the tumors. Similarly, even in tumors where mammalian Asx expression is not aberrant, effecting mammalian Asx upregulation or augmentation of mammalian Asx activity may suppress metastases.

Further objects, features, and advantages of the present invention will become apparent from the detailed description. It should be understood, however, that the detailed description, while indicating preferred embodiments of the invention, is given by way of illustration only, since various changes and modifications within the spirit and scope of the invention will become apparent to those skilled in the art from this detailed description.

Definitions

A "nucleic acid molecule" or a "polynucleotide," as used herein, refers to either RNA or DNA molecule that encodes a specific amino acid sequence or its complementary strand. Nucleic acid molecules may also be non-coding sequences, for example, a ribozyme, an antisense oligonucleotide, or an untranslated portion of a gene. A "coding sequence" as used herein, refers to either RNA or DNA that encodes a specific amino acid sequence or its complementary strand. A polynucleotide may include, for example, an antisense oligonucleotide, or a ribozyme, and may also include such items as a 3' or 5' untranslated region of a gene, or an intron of a gene, or other region of a gene that does not make up the coding region of the gene. The DNA or RNA may be single stranded or double stranded. Synthetic nucleic acids or synthetic polynucleotides can be chemically synthesized nucleic acid sequences, and may also be modified with chemical moieties to render the molecule resistant to degradation. Synthetic nucleic acids can be ribozymes or antisense molecules, for example. Modifications to synthetic nucleic acid molecules include nucleic acid monomers or derivative or modifications thereof, including chemical moieties. For example, phosphothioates can be used for the modification. A polynucleotide derivative can include, for example, such polynucleotides as branched DNA (bDNA). A polynucleotide can be a synthetic or recombinant polynucleotide, and can be generated, for example, by polymerase chain reaction (PCR) amplification, or recombinant expression of complementary DNA or RNA, or by chemical synthesis. Mammalian Asx polynucleotides are at least 70% and preferably at least 75, 80, 85, 90, or 95% identical with either mouse or human hAsx sequences. These can be obtained, inter alia, by hybridization of mouse or human Asx probes under conditions of stringent hybridization. Encompassed within the definition of mammalian, human, and mouse Asx are sequences which contain allelic variants, as well as sequences which differ due to the degeneracy of the genetic code.

The term "functional portion of" as used herein refers to a portion of an mammalian Asx wild-type molecule which retains at least 50% of activity of mammalian Asx. It also encompasses a portion of an mammalian Asx gene having single base substitutions, deletions, or insertions that have no adverse effect on the activity of the molecule. Truncations of mammalian Asx, fragments of Asx, and combinations of fragments of Asx, which retain at least 50% activity are contemplated. Such portions of hAsx may also be fused to other proteins, such as in a gene fusion.

The term "functional" as used herein refers to a gene functional in cancer or differentiation. A molecule is functional if its expression causes, directly or indirectly, an event specifically associated with differentiation, mitosis, oncogenesis, metastasis, or the like.

The term "modulate" as used herein refers to the ability of a molecule to alter the function or expression of another molecule. Thus, modulate could mean, for example, inhibit, antagonize, agonize, upregulate, downregulate, induce, or suppress. A modulator has the capability of altering function of its target. Such alteration can be accomplished at any stage of the transcription, translation, expression or function of the protein, so that, for example, modulation of mammalian Asx can be accomplished by modulation of the DNA, RNA, and protein products of the gene. It assumed that modulation of the function of the target, for example, mammalian Asx, will in turn modulate, alter, or affect the function or pathways leading to a function of genes and proteins that would otherwise associate, and interact, or respond to, mammalian Asx.

A "malignancy" includes any proliferative disorder in which the cells proliferating are ultimately harmful to the host. Cancer is an example of a proliferative disorder that manifests a malignancy. Neoplasia is the state of cells which experience uncontrolled cell growth, whether or not malignant.

The term "regulatory sequence" as used herein refers to a nucleic acid sequence encoding one or more elements that are capable of affecting or effecting expression of a gene sequence, including transcription or translation thereof, when the gene sequence is placed in such a position as to subject it to the control thereof. Such a regulatory sequence can be, for example, a minimal promoter sequence, a complete promoter sequence, an enhancer sequence, an upstream activation sequence ("UAS"), an operator sequence, a downstream termination sequence, a polyadenylation sequence, an optimal 5' leader sequence to optimize initiation of translation, and a Shine-Dalgarno sequence. Alternatively, the regulatory sequence can contain a combination enhancer/promoter element. The regulatory sequence that is appropriate for expression of the present construct differs depending upon the host system in which the construct is to be expressed. Selection of the appropriate regulatory sequences for use herein is within the capability of one skilled in the art. For example, in prokaryotes, such a regulatory sequence can include one or more of a promoter sequence, a ribosomal binding site, and a transcription termination sequence. In eukaryotes, for example, such a sequence can include one or more of a promoter sequence and/or a transcription termination sequence. If any necessary component of a regulatory sequence that is needed for expression is lacking in the polynucleotide construct, such a component can be supplied by a vector into which the polynucleotide construct can be inserted for expression. Regulatory sequences suitable for use herein may be derived from any source including a prokaryotic source, an eukaryotic source, a virus, a viral vector, a bacteriophage or from a linear or circular plasmid. An example of a regulatory sequence is the human immunodeficiency virus ("HIV") promoter that is located in the U3 and R region of the HIV long terminal repeat ("LTR"). Alternatively, the regulatory sequence herein can be a synthetic sequence, for example, one made by combining the UAS of one gene with the remainder of a requisite promoter from another gene, such as the GADP/ADH2 hybrid promoter.

The terms "protein", "polypeptide", "polypeptide derivatives" and modifications and variants thereof refer herein to the expression product of a polynucleotide construct of the invention as defined above. The terms further include truncations, variants, alleles, analogs and derivatives thereof. Unless specifically mentioned otherwise, such mammalian Asx polypeptides possess one or more of the bioactivities of the mammalian Asx protein, such as those discovered herein. This term is not limited to a specific length of the product of the mammalian Asx gene. Thus, polypeptides that are identical or share at least 70%, and more preferably 75%, and most preferably 80, 85, 90, or 95% identity with the mammalian Asx protein or the mature mammalian Asx protein, wherever derived, from human or nonhuman sources are included within this definition of the mammalian Asx polypeptide. Also included, therefore, are alleles and variants of the product of the mammalian Asx gene that contain amino acid substitutions, deletions, or insertions. The amino acid substitutions can be conservative amino acid substitutions or substitutions to eliminate nonessential amino acid residues such as to alter a glycosylation site, a phosphorylation site, an acetylation site, or to alter the folding pattern by altering the position of the cysteine residue that is not necessary for function, etc. Conservative amino acid substitutions are those that preserve the general charge, hydrophobicity/hydrophilicity and/or steric bulk of the amino acid substituted, for example, substitutions between the members of the following groups are conservative substitutions: Gly/Ala, Val/Ile/Leu, Asp/Glu, Lys/Arg, Asn/Gln, Ser/Thr/Cys and Phe/Trp/Tyr. Analogs include peptides having one or more peptide mimics, also known as peptoids, that possess mammalian Asx protein-like activity. Included within the definition are, for example, polypeptides containing one or more analogs of an amino acid (including, for example, unnatural amino acids, etc.), polypeptides with substituted linkages, as well as other modifications known in the art, both naturally occurring and nonnaturally occurring. The term "mammalian Asx" also may include post-expression modifications of the polypeptide, for example, glycosylations, acetylations, phosphorylations, myrstylations, farnesylations, palmitoylations and the like.

The term "polypeptide fragment" as used herein refers to a polypeptide sequence that does not encode the full length of a protein but that is identical to a region of the protein. The fragment is designed to retain the functional aspect of the region of the polypeptide from which it is derived. Two fragments can cooperate to provide function. Two distinct polypeptide fragments of the same gene may represent expressed splice variants of that gene, although functionality and expression of the polypeptide splice variant products may occur in similar biological conditions, and may be related, at least in part, in function.

The term "derivative" as used herein in reference to a polypeptide or a polynucleotide means a polypeptide or polynucleotide that retains at least 50% of the functionality of the polypeptide or polynucleotide to which it is a derivative. They may be variously modified by nucleotide or amino acid deletions, substitutions, insertions or inversions by, for example, site directed mutagenesis of the underlying nucleic acid molecules. Derivatives of a polypeptide or polynucleotide may also be fragments or combinations of fragments thereof. In any case, a derivative, or a fragment, retains at least some, and preferably all of the function of the polypeptide from which it is derived.

An "isolated polypeptide" or "isolated polynucleotide" as used herein refers to a polypeptide or polynucleotide, respectively, produced in vivo or in vitro in an environment manipulated by humans using state of the art techniques of molecular biology, biochemistry and gene therapy. For example, an isolated polypeptide can be produced in a cell free system by automated peptide or polypeptide synthesis, in heterologous host cells transformed with the nucleic acid sequence encoding the polypeptide and regulatory sequences for expression in the host cells, and in an animal into which the coding sequence of the polypeptide has been introduced for expression in the animal. A polypeptide or polynucleotide is "isolated" for purposes herein to the extent that it is not present in its natural state inside a cell as a product of nature. For example, such isolated polypeptides or polynucleotides can be 10% pure, 20% pure, or a higher degree of purity, such as 50%, 75%, 85%, or 90%.

The term "condition" as used herein in terms of "a patient having a condition" refers to a particular state of molecular and cellular systems in a biological context. A biological context includes any organism considered to have life, and for the purposes of this invention includes but is not limited the following organisms or groups: animals, mammals, humans, and vertebrates. A biological condition can include, for example, a disease or a medical condition that may or may not be characterized by identifiable symptoms or indicators. A "condition characterized by abnormal cell proliferation" is most likely a cancer condition, but may also be a condition arising in the development of an organism.

The term "modulator" as used herein describes any moiety capable of changing the endogenous activity or a polypeptide. Modulatory activities can include, for example, modulation at the level of transcription, translation, expression, secretion, or modulation of polypeptide activity inside or outside a cell. Modulation can include, for example, inhibition, antagonism, and agonism, and modulation can include, for example, modulation of upstream or downstream effects that effect the ultimate activities in a pathway, or modulation of the configuration of a polypeptide such that its activity is altered. Modulation can be transitory or permanent, and may be a dose dependent effect.

The term "inhibitor" for use herein can be any inhibitor of a polypeptide activity. The category includes but is not limited to any of the herein described antagonists of mammalian Asx. The inhibitor of mammalian Asx can be an antibody-based mammalian Asx antagonist, or a polypeptide fragment thereof, a peptide mammalian Asx antagonist, a peptoid mammalian Asx antagonist, or a small molecule mammalian Asx antagonist. The polypeptide inhibitor can be one screened from a cDNA, cRNA, or phage display library of polypeptides. The inhibitor can be a polynucleotide, such as, for example a ribozyme or an antisense oligonucleotide, or can be derivatives of these. It is expected that some inhibitors will act at transcription, some at translation, and some on the mature protein. However, the use and appropriateness of such inhibitors of mammalian Asx for the purposes of the invention are not limited to any theories of mechanism of action of the inhibitor. It is sufficient for purposes of the invention that an inhibitor inhibit the activity of mammalian Asx.

The term "antagonist" as used herein refers to a molecule that inhibits or blocks the activity of a polypeptide, either by blocking the polypeptide itself, or by causing a reduced expression of the polypeptide by either blocking transcription of the gene encoding the polypeptide, or by interfering with or destroying a transcription or translation product of the gene. An antagonist may be, for example, a small molecule, peptide, peptoid, polypeptide, or polynucleotide. The polynucleotide may be, for example, a ribozyme, an antisense oligonucleotide, or a coding sequence.

The term "agonist" as used herein refers to a molecule that mimics the activity of the target polypeptide. For example, in the case of mammalian Asx, an agonist could mimic the transcriptional negative regulation capability of mammalian Asx. An agonist may be, for example a small molecule, peptide, peptoid, polypeptide, or polynucleotide.

The term "pharmaceutical composition" refers to a composition for administration of a therapeutic agent, such as antibodies or a polypeptide, or inhibitors or genes and other therapeutic agents listed herein, in vivo, and refers to any pharmaceutical carrier that does not itself induce the production of antibodies harmful to the individual receiving the composition, and which may be administered without undue toxicity.

The term "an effective amount" as used herein refers to an amount that is effective to induce a desired effect. Where the effect is a therapeutic effect, the effective amount is that amount that will accomplish a therapeutic goal, for example, tumor regression, tumor marker reduction, or a positive indication from other indicia of cancer that indicates a reduction or growth slowing of cancer cells. Where the therapeutic agent is, for example, an antagonist of mammalian Asx, the effective amount of the antagonist would be an amount that antagonizes mammalian Asx activity among a population of cells. The amount that is effective depends in part upon the indicia selected for determining effectiveness, and depends upon the effect sought.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance. However, the effective amount for a given situation can be determined by routine experimentation. Administration can include administration of a polypeptide, and causing the polypeptide to be expressed in an animal by administration of the polynucleotide encoding the polypeptide.

A "recombinant vector" herein refers to any vector for transfer or expression of the polynucleotides herein in a cell, including, for example, viral vectors, non-viral vectors, plasmid vectors and vectors derived from the regulatory sequences of heterologous hosts and expression systems.

The term "in vivo administration" refers to administration to a mammal of a polynucleotide encoding a polypeptide for expression in the mammal. In particular, direct in vivo administration involves transfecting a mammal's cell with a coding sequence without removing the cell from the mammal. Thus, direct in vivo administration may include direct injection of the DNA encoding the polypeptide of interest in the region afflicted by the malignancy or proliferative disorder, resulting in expression in the mammal's cells.

The term "ex vivo administration" refers to transfecting a cell, for example, a cell from a population of cells that are malignant or proliferating, after the cell is removed from the mammal. After transfection the cell is then replaced in the mammal. Ex vivo administration can be accomplished by removing cells from a mammal, optionally selecting for cells to transform, (i.e. cells that are malignant or proliferating) rendering the selected cells incapable of replication, transforming the selected cells with a polynucleotide encoding a gene for expression, (i.e. mammalian Asx), including also a regulatory region for facilitating the expression, and placing the transformed cells back into the mammal for expression of the mammalian Asx.

"Biologically active" refers to a molecule that retains a specific activity. A biologically active mammalian Asx polypeptide, for example, retains the activity including for example the control of a homeotic gene or group of homeotic genes.

"Mammalian cell" as used herein refers to a subset of eukaryotic cells useful in the invention as host cells, and includes human cells, and animal cells such as those from dogs, cats, cattle, horses, rabbits, mice, goats, pigs, etc. The cells used can be genetically unaltered or can be genetically altered, for example, by transformation with appropriate expression vectors, marker genes, and the like. Mammalian cells suitable for the method of the invention are any mammalian cell capable of expressing the genes of interest, or any mammalian cells that can express a cDNA library, cRNA library, genomic DNA library or any protein or polypeptide useful in the method of the invention. Mammalian cells also include cells from cell lines such as those immortalized cell lines available from the American Type Culture Collection (ATCC). Such cell lines include, for example, rat pheochromocytoma cells (PC12 cells), embryonal carcinoma cells (P19 cells), Chinese hamster ovary (CHO) cells, HeLa cells, baby hamster kidney (BHK) cells, monkey kidney cells (COS), human hepatocellular carcinoma cells (e.g., Hep G2), human embryonic kidney cells, mouse sertoli cells, canine kidney cells, buffalo rat liver cells, human lung cells, human liver cells, mouse mammary tumor cells, as well as others. Also included are hematopoetic stem cells, neuronal stem cells such as neuronal sphere cells, and embryonic stem cells (ES cells).

The present invention will now be illustrated by reference to the following examples which set forth particularly advantageous embodiments. However, it should be noted that these embodiments are illustrative and are not to be construed as restricting the invention in any way.

EXAMPLE 1

A small molecule modulator of hAsx is identified and incorporated into a pharmaceutical composition including a liposomal-based pharmaceutically acceptable carrier for administration to a cancer patient for controlling the expression or activity of hAsx in the patient. Administration the composition is achieved by injection into the tumor tissue. The patient is monitored for reduction of hAsx activity as a diagnostic marker evaluating the effectiveness of the treatment.

EXAMPLE 2

A population of progenitor cells are treated with a functional portion of recombinant hAsx polypeptide and induced to differentiate. The differentiation is identified by a differential display of mRNA transcripts of a treated and untreated population of cells. The process is reversed by administering to the population of cells an inhibitor of hAsx activity, and likewise assayed by the differential display of mRNA transcripts of the two populations. The process can be monitored by differential display of mRNA transcripts of the cells.

EXAMPLE 3

Poly A$^+$ RNA was isolated from normal and cancer cell lines. The mRNA was electrophoretically fractionated and transferred to a nylon filter. The mRNA on the filter was immobilized by UV crosslinking. A labeled probe was prepared from the sequence of SEQ ID NO: 1, labeled with $^{32}$P radionucleotide, and used in a hybridization reaction with the RNA on the filter under stringent conditions.

The filter was allowed to hybridize to the probe, and the unbound probe was washed from the filter. The hybridization was conducted using standard techniques for Northern hybridizations, for example, as described in Sambrook et al. (1989), MOLECULAR CLONING: A LABORATORY MANUAL, 2nd ed. (Cold Spring Harbor Press, Cold Spring Harbor, N.Y.).

Exposure of the filter to X-ray film showed pronounced bands in the cancer cell lines, and very little activity in the normal cell lines. Beta actin was used as a control to normalize expression levels in the cell lines.

The normal tissues probed were human adult heart, skeletal muscle, pancreas, prostate, testes, ovary, colon, thymus, brain, placenta, lung, liver, kidney, peripheral leukocytes, and spleen. The tissue specific expression of hAsx in normal human adult tissue indicated moderate hAsx transcript in human testes, ovary and thymus. Nondetectable or very low quantities of transcript were present in the other tissues including human prostate, colon, brain, placenta, lung, liver, and kidney, leukocytes, and spleen. Two transcripts, one at about 7.5 kilobases, and one at about 5.5 kilobases were observed in the testes, and only the larger transcript was observed in the ovary and thymus tissues.

By contrast, hAsx transcripts were present at a very high level in the following human cancer cell lines: promyelocytic leukemia HL-60, HeLa cell S3, chronic myelogenous leukemia K-562, lymphoblastic leukemia MOLT4, Burkitt's lymphoma Raji, colorectal adenocarcinoma SW480, and melanoma G361. In addition, hAsx transcript was also abundantly expressed in other colorectal adenocarcinoma tissue, and lymphocytic cancer tissues. Expression was very low in the lung cancer cell line A549. The hAsx transcripts were about 7.5–8.5 kilobases and about 5.5–6.5 kilobases in all these cell lines for all hybridizations. Hybridizations were conducted using stringent conditions and a standard hybridization protocol for accomplishing Northern blot hybridizations.

Transcript levels were controlled for by probing with actin probe on the same blots probed with hAsx coding sequence.

EXAMPLE 5

A human P1 genomic clone was obtained from a P1 filter library using an hAsx cDNA as a probe. After DNA preparation, the identity of the clone was confirmed by sequencing a PCR product generated from the Asx P1 clone. Sequence matching hAsx exon sequence was interrupted by nonexonic sequence. Consensus splice donor and acceptor sites were present at the intron-exon boundaries. The hAsx genomic clone was labeled and used as a probe against human metaphase chromosomes. FISH mapping showed that hAsx maps to 20q11.

The description of the invention draws on previously published work and, at times, on pending patent applications. By way of example, such work consists of scientific papers, abstracts, or issued patents, and published patent applications. All published work cited herein are hereby incorporated by reference.

The following sequences are described below:

SEQ ID NO: 1 is the human cDNA sequence for Asx
SEQ ID NO: 2 is the translated human amino acid sequence for Asx
SEQ ID NO: 3 is the mouse cDNA for Asx
SEQ ID NO: 4 is the translated mouse amino acid sequence for Asx

What is claimed is:

1. An isolated nucleic acid molecule which encodes a mammalian Asx polypeptide comprising the amino acid sequence shown in SEQ ID NO:2.

2. The nucleic acid molecule of claim 1 which comprises the nucleotide sequence shown in SEQ ID NO:1.

3. A vector comprising the nucleic acid molecule of claim 1.

4. A vector comprising the nucleic acid molecule of claim 2.

5. The vector of claim 3 which is a viral vector.

6. The vector of claim 3 which is a non-viral vector.

7. The vector of claim 4 which is a viral vector.

8. The vector of claim 4 which is a non-viral vector.

9. A host cell comprising an isolated nucleic acid molecule which encodes a mammalian Asx polypeptide comprising the amino acid sequence shown in SEQ ID NO:2.

10. The host cell of claim 9 wherein the isolated nucleic acid molecule comprises the nucleotide sequence shown in SEQ ID NO:1.

11. The host cell of claim 9 which is selected from the group consisting of bacterial, yeast, insect, amphibian, and mammalian cells.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 4926 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CGCCCGGGCC CCCCTCGCGG GGGACCGTGC CCCCGCCGCC GGGGCGAAGG ATGAAGGACA      60

AACAGAAGAA GAAGAAGGAG CGCACGTGGG CCGAGGCCGC GCGCCTGGTA TTAGAAAACT     120

ACTCGGATGC TCCAATGACA CCAAAACAGA TTCTGCAGGT CATAGAGGCA GAAGGACTAA     180

AGGAAATGAG AAGTGGGACT TCCCCTCTCG CATGCCTCAA TGCTATGCTA CATTCCAATT     240

CAAGAGGAGG AGAGGGGTTG TTTTATAAAC TGCCTGGCCG AATCAGCCTT TTCACGCTCA     300

AGAAGGATGC CCTGCAGTGG TCTCGCCATC CAGCTACAGT GGAGGGAGAG GAGCCAGAGG     360

ACACGGCTGA TGTGGAGAGC TGTGGGTCTA ATGAAGCCAG CACTGTGAGT GGTGAAAACG     420

ATGTATCTCT TGATGAAACA TCTTCGAACG CATCCTGTTC TACAGAATCT CAGAGTCGAC     480

CTCTTTCCAA TCCCAGGGAC AGCTACAGAG CTTCCTCACA GGCGAACAAA CAAAAGAAAA     540

AGACTGGGGT GATGCTGCCT CGAGTTGTCC TGACTCCTCT GAAGGTAAAC GGGGCCCACG     600

TGGAATCTGC ATCAGGGTTC TCGGGCTGCC ACGCCGATGG CGAGAGCGGC AGCCCGTCCA     660

GCAGCAGCAG CGGCTCTCTG GCCCTGGGCA GCGCTGCTAT TCGTGGCCAG GCCGAGGTCA     720

CCCAGGACCC TGCCCCGCTC CTGAGAGGCT TCCGGAAGCC AGCCACAGGT CAAATGAAGC     780
```

-continued

```
GCAACAGAGG GGAAGAAATA GATTTTGAGA CACCTGGGTC CATTCTTGTC AACACCAACC      840

TCCGTGCCCT GATCAACTCT CGGACCTTCC ATGCCTTACC ATCACACTTC CAGCAGCAGC      900

TCCTCTTCCT CCTGCCTGAA GTAGACAGAC AGGTGGGGAC GGATGGCCTG TTGCGTCTCA      960

GCAGCAGTGC ACTAAATAAC GAGTTTTTTA CCCATGCGGC TCAGAGCTGG CGGGAGCGCC     1020

TGGCTGATGG TGAATTTACT CATGAGATGC AAGTCAGGAT ACGACAGGAA ATGGAGAAGG     1080

AAAAGAAGGT GGAACAATGG AAAGAAAAGT TCTTTGAAGA CTACTATGGA CAGAAGCTGG     1140

GTTTGACCAA AGAAGAGTCA TTGCAGCAGA ACGTGGGCCA GGAGGAGGCT GAAATCAAAA     1200

GTGGCTTGTG TGTCCCAGGA GAATCAGTGC GTATACAGCG TGGTCCAGCC ACCCGACAGC     1260

GAGATGGGCA TTTTAAGAAA CGCTCTCGGC CAGATCTCCG AACCAGAGCC AGAAGGAATC     1320

TGTACAAAAA ACAGGAGTCA GAACAAGCAG GGGTTGCTAA GGATGCAAAA TCTGTGGCCT     1380

CAGATGTTCC CCTCTACAAG GATGGGAGA CTAAGACTGA CCCAGCAGGG CTGAGCAGTC     1440

CCCATCTGCC AGGCACATCC TCTGCAGCAC CCGACCTGGA GGGTCCCGAA TTCCCAGTTG     1500

AGTCTGTGGC TTCTCGGATC CAGGCTGAGC CAGACAACTT GGCACGTGCC TCTGCATCTC     1560

CAGACAGAAT TCCTAGCCTG CCTCAGGAAA CTGTGGATCA GGAACCCAAG GATCAGAAGA     1620

GGAAATCCTT TGAGCAGGCG GCCTCTGCAT CCTTTCCCGA AAAGAAGCCC CGGCTTGAAG     1680

ATCGTCAGTC CTTTCGTAAC ACAATTGAAA GTGTTCACAC CGAAAAGCCA CAGCCCACTA     1740

AAGAGGAGCC CAAAGTCCCG CCCATCCGGA TTCAACTTTC ACGTATCAAA CCACCCTGGG     1800

TGGTTAAAGG TCAGCCCACT TACCAGATAT GCCCCCGGAT CATCCCCACC ACGGAGTCCT     1860

CCTGCCGGGG TTGGACTGGC GCCAGGACCC TCGCAGACAT TAAAGCCCGT GCTCTGCAGG     1920

TCCGAGGGGC GAGAGGTCAC CACTGCCATA GAGAGGCGGC CACCACTGCC ATCGGAGGGG     1980

GGGGTGGCCC GGGTGGAGGT GGCGGCGGGG CCACCGATGA GGGAGGTGGC AGAGGCAGCA     2040

GCAGTGGTGA TGGTGGTGAG GCCTGTGGCC ACCCTGAGCC CAGGGGAGGC CCGAGCACCC     2100

CTGGAAAGTG TACGTCAGAT CTACAGCGAA CACAACTACT GCCGCCTTAT CCTCTAAATG     2160

GGGAGCATAC CCAGGCCGGA ACTGCCATGT CCAGAGCTAG GAGAGAGGAC CTGCCTTCTC     2220

TGAGAAAGGA GGAAAGCTGC CTACTACAGA GGGCTACAGT TGGACTCACA GATGGGCTAG     2280

GAGATGCCTC CCAACTCCCC GTTGCTCCCA CTGGGGACCA GCCATGCCAG GCCTTGCCCC     2340

TACTGTCCTC CCAAACCTCA GTAGCTGAGA GATTAGTGGA GCAGCCTCAG TTGCATCCGG     2400

ATGTTAGAAC TGAATGTGAG TCTGGCACCA CTTCCTGGGA AAGTGATGAT GAGGAGCAAG     2460

GACCCACCGT TCCTGCAGAC AATGGTCCCA TTCCGTCTCT AGTGGGAGAT GATACATTAG     2520

AGAAAGGAAC TGGCCAAGCT CTTGACAGTC ATCCCACTAT GAAGGATCCT GTAAATGTGA     2580

CCCCCAGTTC CACACCTGAA TCCTCACCGA CTGATTGCCT GCAGAACAGA GCATTTGATG     2640

ACGAATTAGG GCTTGGTGGC TCATGCCCTC CTATGAGGGA AAGTGATACT AGACAAGAAA     2700

ACTTGAAAAC CAAGGCTCTC GTTTCTAACA GTTCTTTGCA TTGGATACCC ATCCCATCGA     2760

ATGATGAGGT AGTGAAACAG CCCAAACCAG AATCCAGAGA ACACATACCA TCTGTTGAGC     2820

CCCAGGTTGG AGAGGAGTGG GAGAAAGCTG CTCCCACCCC TCCTGCATTG CCTGGGGATT     2880

TGACAGCTGA GGAGGGTCTA GATCCTCTTG ACAGCCTTAC TTCACTCTGG ACTGTGCCAT     2940

CTCGAGGAGG CAGTGACAGC AATGGCAGTT ACTGTCAACA GGTGGACATT GAAAAGCTGA     3000

AAATCAACGG AGACTCTGAA GCACTGAGTC CTCACGGTGA GTCCACGGAT ACAGCCTCTG     3060

ACTTTGAAGG TCACCTCACG GAGGACAGCA GTGAGGCTGA CACTAGAGAA GCTGCAGTGA     3120

CAAAGGGATC TTCGGTGGAC AAGGATGAGA AACCCAATTG GAACCAATCT GCCCCACTGT     3180
```

```
CCAAGGTGAA TGGTGACATG CGTCTGGTTA CAAGGACAGA TGGGATGGTT GCTCCTCAGA    3240

GCTGGGTGTC TCGAGTATGT GCGGTCCGCC AAAAGATCCC AGATTCCCTA CTGCTGGCCA    3300

GTACTGAGTA CCAGCCAAGA GCCGTGTGCC TGTCCATGCC TGGGTCCTCA GTGGAGGCCA    3360

CTAACCCACT TGTGATGCAG TTGCTGCAGG GTAGCTTGCC CCTAGAGAAG GTTCTTCCAC    3420

CAGCCCACGA TGACAGCATG TCAGAATCCC ACAAGTACC ACTTACAAAA GACCAGAGCC     3480

ATGGCTCGCT ACGCATGGGA TCTTTACATG GTCTTGGAAA AACAGTGGC ATGGTTGATG     3540

GAAGCAGCCC CAGTTCTTTA AGGGCTTTGA AGGAGCCTCT TCTGCCAGAT AGCTGTGAAA    3600

CAGGCACTGG TCTTGCCAGG ATTGAGGCCA CCCAGGCTCC TGGAGCACCC CAAAAGAATT    3660

GCAAGGCAGT CCCAAGTTTT GACTCCCTCC ATCCAGTGAC AAATCCCATT ACATCCTCTA    3720

GGAAACTGGA AGAAATGGAT TCCAAAGAGC AGTTCTCTTC CTTTAGTTGT GAAGATCAGA    3780

AGGAAGTCCG TGCTATGTCA CAGGACAGCA ATTCAAATGC TGCTCCAGGA AAGAGCCCAG    3840

GAGATCTTAC TACCTCGAGA ACACCTCGTT TCTCATCTCC AAATGTGATC TCCTTTGGTC    3900

CAGAGCAGAC AGGTCGGGCC CTGGGTGATC AGAGCAATGT TACAGGCCAA GGGAAGAAGC    3960

TTTTTGGCTC TGGGAATGTG GCTGCAACCC TTCAGCGCCC CAGGCCTGCG ACCCGATGC     4020

CTCTTCCTGC TGAGATCCCT CCAGTTTTTC CCAGTGGGAA GTTGGGACCA AGCACAAACT    4080

CCATGTCTGG TGGGGTACAG ACTCCAAGGG AAGACTGGGC TCCAAAGCCA CATGCCTTTG    4140

TTGGCAGCGT CAAGAATGAG AAGACTTTTG TGGGGGGTCC TCTTAAGGCA AATGCCGAGA    4200

ACAGGAAAGC TACTGGGCAT AGTCCCCTGG AACTGGTGGG TCACTTGGAA GGGATGCCCT    4260

TTGTCATGGA CTTGCCCTTC TGGAAATTAC CCCGAGAGCC AGGGAAGGGG CTCAGTGAGC    4320

CTCTGGAGCC TTCTTCTCTC CCCTCCCAAC TCAGCATCAA GCAGGCATTT TATGGGAAGC    4380

TTTCTAAACT CCAACTGAGT TCCACCAGCT TTAATTATTC CTCTAGCTCT CCCACCTTTC    4440

CCAAAGGCCT TGCTGGAAGT GTGGTGCAGC TGAGCCACAA AGCAAACTTT GGTGCGAGCC    4500

ACAGTGCATC ACTTTCCTTG CAAATGTTCA CTGACAGCAG CACGGTGGAA AGCATCTCGC    4560

TCCAGTGTGC GTGCAGCCTG AAAGCCATGA TCATGTGCCA AGGCTGCGGT GCGTTCTGTC    4620

ACGATGACTG TATTGGACCC TCAAAGCTCT GTGTATTGTG CCTTGTGGTG AGATAATAAA    4680

TTATGGCCAT GGGAAACGTT GTATATTTAG TGTGTGTATT TGATAATGA TTGATCTTAA     4740

ATCTGTATAC AGAATATCAT TGATACAATA CTCTTTAGGC AGGAGCACTC TTGCCTTCCC    4800

CCAAAATTTA CACTGCTAAA GCCCTCTGTC ACTTGGCGAC CCTTCTGGTC TTGCTGGAGG    4860

GGTTTCCTGG GTATAACCCA TTGGGCTGCC CAAGGCCAGC CAGCCTGAGC TCTCCTGCAA    4920

GACAGG                                                              4926
```

(2) INFORMATION FOR SEQ ID NO:2:

(i) SEQUENCE CHARACTERISTICS:
        (A) LENGTH: 903 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Val Gln His Asp Trp Asn Phe Gly Asp Ile Lys Leu Ser Ser Ser Gln
 1               5                  10                  15

Ser Ser Gly Asp Gln Gln Arg Asn Leu Ser His Glu Ala Ile Asp Leu
            20                  25                  30

Met Asp Val Val Gln Asp Ala Asp Val Ile Asp Asp Ile Met His Asn
```

```
                35                  40                  45
Asp Val Cys His Asp Val Leu Gly Asp Glu Asp Gly Asp Gln Glu
     50                  55                  60
Glu Asp Glu Asp Glu Val Val Glu Cys Met Thr Glu Glu Gln Gln
 65                  70                  75                  80
Leu Ile Asp Glu Asp Ser Glu Ala Val Arg Glu Ile Val Asp Lys Leu
                 85                  90                  95
Gln Gln His Gln Gln Gln Asn Gln Gln Gln His His Gln Gln Leu
                100                 105                 110
His Ile Gln Asp Val Val Gln Leu Ala Gln His Ser Phe Met Pro Gln
             115                 120                 125
Ala His Ser Glu Phe Gly Asn Asp Ile Gly Gln Glu Met Leu Cys Asp
 130                 135                 140
Ala Val Pro Met Ser Ala Ala Glu Met Glu Val Ser Ser Thr Val Ile
 145                 150                 155                 160
Thr Asn Ser Ser Asn Ser Asn Asp Ser Ser Asn Asn Ile Ser Leu Cys
                 165                 170                 175
Ser Ser Thr Asn Ser Leu Thr Ile Asn Gln Met Pro His Gln Ala Ser
             180                 185                 190
Gln Gln Pro Gln Gln Asn Ala Gln Ser Asn Ala Gln Gln Gln Arg Gln
             195                 200                 205
Ile Leu Val Asp Ser Asn Gly Gln Ile Ile Gly Asn Phe Leu Leu Gln
 210                 215                 220
Gln Gln Arg Gln Gln Gln Gln Gln Leu Leu Gln Gln Phe Thr Leu
225                 230                 235                 240
Gln Ala Ala Ala Ala Gln Gln Gln Gln Gln Gln Gln Gln His Gln
                 245                 250                 255
Gln Gln Gln Gln Gln Gln Gln Ala Thr Ser Ser Asn Ser Leu Gly
             260                 265                 270
Lys Thr Leu Pro Val Ala Leu Arg Asn Gly Thr Gln Gln Phe Leu Ser
             275                 280                 285
Pro Asn Leu Ile Ala Gln Gln His Gln Gln Gln Gln Gln Gln Leu
 290                 295                 300
Glu Gln His Gln Gln Gln Ala Thr Ala Gln Gln Lys His Gln Gln Ile
 305                 310                 315                 320
Gln Gln Phe Ala Leu Gln Gln Ala Gln Leu His Gln Arg Gln Leu Leu
             325                 330                 335
Ala Gln Ala Ala Asn Asn Asn Leu Leu Gln Gln Gln Gln Gln Gln
                 340                 345                 350
Gln Asn Val Ala Leu Pro Thr Thr Gln Ala Lys Phe Ile Ala Lys Pro
             355                 360                 365
Leu Asn Ile Ile Ser Met Thr Arg Pro Ala Asn Ala Ser Pro Thr Thr
 370                 375                 380
Ala Ala Thr Thr Ala Asn Thr Ala Ser Ile Pro Ser Ala Tyr Ala Asn
 385                 390                 395                 400
Val Val Ala Val Thr Gly Ala Gln Gln Gln Ser Pro Pro Val Pro
                 405                 410                 415
Ala Pro Gln Gln Gln Thr Val Gln Gln Gln Leu Ala Asn His Asn
             420                 425                 430
Ser Asn Met Gln Gln Leu Pro Asn Val Leu Thr Met Lys Thr Leu Pro
             435                 440                 445
Pro Ser Gly Val Pro Thr Thr Ile Ala Gln Gln Arg Leu Gln Pro Lys
 450                 455                 460
```

```
Met Pro Thr Gly Lys Gly Arg Lys Ala Thr Ser Asn Arg Leu Pro Pro
465                 470                 475                 480

Gly Ala Val Asn Leu Glu Arg Thr Tyr Gln Ile Cys Gln Ala Val Ile
            485                 490                 495

Gln Asn Ser Pro Asn Arg Glu Asn Leu Lys Ala Gln Leu Arg Pro Pro
        500                 505                 510

Ala Ala Ile Leu Asn Gln His Gln Pro Thr Thr Thr Ala Pro Ala
        515                 520                 525

Pro Ile Asn Pro Val Thr Leu Asn Val Ser Thr Val Ala Ala Thr Pro
530                 535                 540

Met Ser Asn Ile Thr Thr Ala Thr Gly Ser Met Ala Ala Val Ala
545                 550                 555                 560

Ala Ala Pro Pro Gln Asn Val Leu Lys Gln Glu Glu Leu Leu Val Ser
            565                 570                 575

Gly Ala Val Gly Ala Gly Ala Leu Pro Ala Gly Leu Pro Pro Asn Val
            580                 585                 590

Met Gly Val Gly Arg Pro Gly Val Tyr Lys Val Ile Gly Pro Arg Met
            595                 600                 605

Ser Gly Phe Pro Arg Lys Lys Tyr Val Gln Arg Lys Pro Ser Pro Thr
        610                 615                 620

Thr Leu Ile Arg His Val Phe Ser Pro Gly Pro Gly Gly Ala Thr Ala
625                 630                 635                 640

Thr Ala Gln Gln Leu Gln Met Leu Gln Gln His His Gln Ser Thr Thr
                645                 650                 655

Ser Pro Val Pro Val Gln Asn Pro Gln Gln Pro Ala Pro Glu Gln Leu
            660                 665                 670

Ile His Gln Asn Gly Asn Gly Gln Tyr Val Leu Val His Arg Ala Asn
        675                 680                 685

Val Gly Ala Ala Asp Asn Gln Ala Pro Arg Ala Ser Ser Ala Pro Pro
    690                 695                 700

Met His Gln Asn Gln Phe Val Thr Val Gln Asn Pro Leu His Ser Ile
705                 710                 715                 720

Asn Gly Ile Pro Met Gly Gly Arg Gly Arg Pro Ala Ser Val Asp Thr
                725                 730                 735

Thr Ala Gly Ser Gly Asn Val Ile Ala Pro Pro Ile Ser Ala Thr Asp
            740                 745                 750

Ala Leu His His His His Glu Met Gln Gln Gln Gln His Gln Gln
        755                 760                 765

Pro Gln Pro Leu Gly Asn Val Gly Ala Ala Ala Asn Ile Val Arg Arg
        770                 775                 780

Asn Ile Ala Ala Gly Pro Asn Ile Ala Tyr Ile Asp Gly Ser Asn Thr
785                 790                 795                 800

Asn Ser Ser Ala Val Ala Leu Met Glu Ala Gly Asn Asn Tyr Ile Val
            805                 810                 815

Thr Thr Asn Ala Ser Pro Thr Ala Ala Pro Ser Pro Ile Asn Gln Gln
            820                 825                 830

Pro Gln Ser Gln Pro Thr Gly Thr Gln His Gln His Pro Leu Leu Gln
        835                 840                 845

Leu His Gln Thr Gly Glu Asn Thr Pro Pro Gly Asn Glu Ala Thr Ala
    850                 855                 860

Thr Ala Asn Asn Cys Ala Cys Ser Leu Asn Ala Met Val Ile Cys Gln
865                 870                 875                 880

Gln Cys Gly Ala Phe Cys His Asp Asp Cys Ile Gly Ala Ala Lys Leu
            885                 890                 895
```

Cys Val Ala Cys Val Ile Arg
            900

(2) INFORMATION FOR SEQ ID NO:3:

(i) SEQUENCE CHARACTERISTICS:
        (A) LENGTH: 5362 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
AAGCTTGATA TCGAATTCGG CACGAGACCG CCCCAGTCCG CCCCGCCCGA AGGACCCGCG      60

TGGAGCCGCC ACCGCCGCCG CGGAGGAGGA GGATGAAGGA CAAACAGAAG AGGAAGAAGG     120

AGCGCACGTG GGCCGAGGCC GCGCGCCTGG TGTTAGAAAA CTACTCAGAT GCTCCAATGA     180

CACCAAAACA GATTCTGCAG GTCATAGAGG CAGAAGGACT GAAGGAAATG AGAAGTGGGA     240

CATCCCCTCT TGCGTGCCTC AATGCCATGC TACATTCCAA CTCAAGAGGA GGAGAAGGGC     300

TGTTTTATAA ATTACCTGGC CGCATTAGTC TTTTCACACT CAAGAAAGAT GCAGTGCAGT     360

GGTCTAGAAA TGCAGCTACA GTGGATGGAG ACGAGCCAGA GGACTCCGCT GATGTGGAAA     420

GCTGTGGGTC TAATGAAGCC AGCACTGTGA GTGGTGAAAA TGATGTATCT CTGGATGAAA     480

CATCTTCAAA TGCATCCTGC TCTACAGAGT CTCAGAGCCG ACCCCTCTCC AATCCCAGGG     540

ACAGCCACAG GGCTTCCTCA CAGGCAAACA ACAGAAGAA AAGGACTGGG GTTATGCTAC     600

CTCGTGTTGT CCTGACTCCT CTGAAGGTAA ACGGGGCCCA CGTGGAACCT GCGTCAGGAT     660

TCTCAGGCCG CCACGCAGAT GGCGAGAGTG GCAGTCCATC GAGCAGCAGC AGCGGTTCTC     720

TGGCCTTGGG CAACAGTGCC ATTCGAGGCC AGGCCGAGGT CACTCGGGAC CCTGCCCCCC     780

TCTTAAGAGG CTTCCGGAAG CCAGCCACAG GGCAAATGAA GCGCAACAGA GGGGAAGAGG     840

TAGATTTTGA GACGCCTGGG TCCATTCTTG TTAACACCAA CCTCCGTGCT CTGATAAACT     900

CTCGGACCTT CCATGCCCTG CCACTACACT TCCAGCAGCA ACTCCTCCTC CTCCTGCCTG     960

AAGTGGACAG ACAGGTGGGG ACAGATGGCC TGCTGCGCCT CAGCGGCAGT GCACTCAATA    1020

ATGAGTTTTT CACCCATGCA GCTCAGAGCT GGCGAGAACG CCTTGCTGAT GGTGAATTCA    1080

CTCATGAGAT GCAAGTCAGG CTAAGACAGG AAATGGAAAA GGAGAAGAAG GTGGAACAAT    1140

GGAAGGAAAA GTTCTTTGAA GATTACTACG ACAGAAATT GGGTTTGACC AAAGAAGAAT    1200

CACTGCAGCA GAAAGAGGTC CAGGAGGAGG CCAAAGTCAA GAGTGGTTTA TGTGTCTCTG    1260

GAGAGTCTGT GCGGCCGCAG CGTGGGCCCA ACACCCGTCA ACGGGACGGA CATTTTAAGA    1320

AACGTTCTCG GCCAGATCTC CGAACCAGAT CCAGAAGGAA TATATACAAA AAACAGGAGC    1380

CAGAACAAGC AGGGGTTGCT AAAGATGCAA GTGCTGCACC AGACGTCTCA CTCTCTAAAG    1440

ATACTAAAAC CGACTTAGCA GGGGTGAACA GTACCCCTGG GCCAGATGTG TCCTCAGCAA    1500

CATCTGGACA GGAGGGTCCC AAGTGTCCCA GTGAACCTGT GGCTTCCCAG ATCCAAGCAG    1560

AAAGGGACAA CTTGGCATGT GCCTCTGCAT CTCCAGACAG AATCCCTACC TTACCTCAGG    1620

ACACTGTGGA TCAAGAGACA AAGGATCAGA AGAGAAAATC CTTTGAGCAG GAAGCCTCTG    1680

CATCCTTTCC CGAAAAGAAA CCCCGGCTTG AAGATCGTCA GTCCTTTCGT AACACAATTG    1740

AAAGTGTTCA CACCGAAAAG CCACAGCCCA CTAAAGAGGA GCCCAAAGTC CGCCCATCC    1800

GGATTCAACT TTCACGTATC AAACCACCCT GGGTGGCTAA AGGTCGGCCC ACTTACCAGA    1860

TATGCCCCCG GATCGTCCCC ATCACGGAGT CCTCCTGCCG GGGTTGGACT GGTGCCAGGA    1920
```

-continued

| | |
|---|---|
| CCCTCGCAGA CATTAAAGCC CGTGCTTTGC AGGCCCGAGG GGCGAGAGGT TACCACTGCA | 1980 |
| ATCGAGAGAC GGCCACCACT GCCATCGGAG GGGGGGGTGG CCCGGGTGGA GGTGGCAGTG | 2040 |
| GGGCCATCGA TGAGGGAGGT GGCAGAGACA GCAGCAGTGG TGATGGTAGT GAGGCCTGTG | 2100 |
| GCCACCCTGA GCCCAGGGGA GCCCCAAGCA CCTCTGGAGA GAGTGCGTCA GATCTACAGC | 2160 |
| GAACACAACT ACTGCCGCCT TGTCCTCTGA ATGGAGAGCA CACTCCAGCT GAAGCTGCCA | 2220 |
| TGCCCAGAGC CAGAAGAGAA GACTCAGCTT CTCTCAGAAA GGAAGAGAGC TGCCTGTTGA | 2280 |
| AGAGGGTCCC AGGTGTGCTT ACAAGTGGGC TGGAAGATGC CTCTCAACCC CCTATTGCTC | 2340 |
| CCACTGGAGA CCAGCCGTGT CAGGCTTTGC CCCCTCTGTC CTCCCAAACT CCAGTGGCCG | 2400 |
| AGATGTTAAC AGAGCAGCCT AAGTTGCTTC TAGATGATAG AACTGAGTGT GAATCTAGTA | 2460 |
| GAGAAGATCA AGGACCCACC ATTCCCTCAG AGAGTAGTTC TGGACGGTTT CCATTGGGAG | 2520 |
| ATCTATTAGG AGGAGGAAGT GACCAGGCCT TTGATAATAT GAAGGAGCCT GTAAGTATGA | 2580 |
| CACCTACTTT TATATCTGAA TTGTCATTAG CTAACTACCT ACAGGATAGG CCTGATGATG | 2640 |
| ATGGATTAGG GCTTGGTGCC ACAGGCCTAC TCATAAGGGA AAGTAGTAGA CAAGAAGCTT | 2700 |
| TGACTGAGGC TTTTGCATCT GGCAGTCCTA CCTCCTGGGT ACCCATTCTG TCAAATTATG | 2760 |
| AGGTAATAAA AACATCTGAT CCAGAATCCA GAGAAAACAT ACCATGTCCG GAGCCCCAGG | 2820 |
| ATGAAAAAGA GTGGGAGAGA GCTGTTCCTC TCATTGCAGC AACAGAAAGT GTGCCCCAAC | 2880 |
| CTGAGAGCTG CATTTCACAT TGGACACCTC CTCCAGCAGC TGTGGGCAGC ACTGGCAGTG | 2940 |
| ACAGTGAGCA AGTGGACCTT GAAAGACTGG AAATGAATGG CATCTCTGAA GCACCAAGTC | 3000 |
| CTCACAGTGA ATCCACAGAT ACAGCCTCTG ACTCCGAAGG CCATCTCTCT GAGGACAGCA | 3060 |
| GTGAGGTTGA TGCAAGTGAA GTCACAGTGG TAAAAGGGTC ATTAGGTGGG GATGAAAAGC | 3120 |
| AAGACTGGGA CCCATCTGCC TCACTGTCCA AGGTGAACAA TGACCTAAGT GTGCTTACAA | 3180 |
| GGACAGGAGG GGTGGCTGCT TCTCAGAGCT GGGTGTCTAG AGTATGTTCA GTCCCACACA | 3240 |
| AGATCCCAGA CTCTCTGTTG CTGTCCAGTA CTGAGTGCCA GCCGAGGTCT GTGTGCCCAC | 3300 |
| TGAGGCCTGG CTCTTCAGTG GAGGTTACCA ACCCACTTGT GATGCACCTG CTGCATGGTA | 3360 |
| ATTTGCCCTT GGAGAAGGTT CTTCCTCCAG GTCACAGAAG CAGCCGACTA GAGTCATCAC | 3420 |
| AGCTGCCACT TAGAGAACAG AGCCAGGATA GAGGCACTCT ACAAGGTACA GGGGAAAACA | 3480 |
| ATCGCCTAGC TGCCAGAATC AACCCTGGTT CTGCACAAAC ATTGAAAGAG TCTATTCTGG | 3540 |
| CCCAGAGCTA TGGAGCAAGT GCTGGTCTTG TCAGGGCAAT GGCCTCCAAG GCTCCTGCAA | 3600 |
| TGTCCCAGAA GATTGCGAAG ATGGTTACAA GTTTAGACTC ACAGCATCCA GAGACAGAAC | 3660 |
| TGACACCTTC CTCTGGCAAT CTGGAAGAAA TAGATTCCAA AGAGCATCTC TCTTCCTTCC | 3720 |
| TTTGTGAAGA GCAGAAAGAA GGCCATTCCC TGTCTCAAGG CAGTGATCCA GGTGCGGCCC | 3780 |
| CAGGCCAATG TCTAGGAGAT CACACTACCT CCAAAGTGCC ATGTTTCTCC TCCACAAATG | 3840 |
| TGAGCCTCTC CTTTGGATCT GAGCAGACAG ATGGGACCCT GAGTGATCAG AACAATGCTG | 3900 |
| GTGGTCATGA AAAGAAACTA TTTGGTCCCG GAATACAGT TACCACCCTT CAGTGCCCCA | 3960 |
| GGTCTGAAGA GCAGACACCA CTACCTGCTG AGGTCCCTCC AGTGTTTCCC AGTAGGAAGA | 4020 |
| TAGAACCAAG CAAAAACTCT GTGTCTGGTG GTGTGCAAAC TACAAGGGAA AACAGGATGC | 4080 |
| CCAAACCACC TCCTGTCTCT GCTGACAGCA TCAAGACAGA GCAGACATTT TGAGGGATC | 4140 |
| CTATTAAGGC AGATGCAGAG AACAGAAAAG CTGCAGGGTA CAGTTCTCTG GAACTAGTGG | 4200 |
| GTCACTTGCA AGGGATGCCT TTTGTTGTGG ATCTGCCTTT CTGGAAGTTA CCCAGAGAGC | 4260 |
| CAGGGAAAGG GTTCAGTCAA CCCCTGGAGC CTTCTTCCAT CCCTTCCCAA CTCAACATCA | 4320 |

```
AGCAGGCCTT GTATGGGAAG TTGTCTAAAC TTCAGCTCAG TCCCACCAGC TTTAATTACT      4380

CCTCTAGCTC TGCTACCTTT CCCAAAGGCC TTGCTGGTGG TGTGGTGCAG CTGAGCCACA      4440

AAGCCAGCTT TGGTACAGGC CACACTGCAT CACTGTCCTT ACAAATGTTC GCTGACAGCA      4500

GTGCAGTAGA AAGCATCTCT CTCCAATGTG CATGCAGCCT GAAAGCCATG ATCATGTGCC      4560

AAGGCTGCGG AGCATTCTGC CATGATGACT GCATTGGACC TTCAAAGCTC TGTGTATTGT      4620

GCCTTGTGGT GAGATAATAA ATTATGGCCA TTGGAAACAT TGTACATTTA GTGTGTGTAT      4680

TTTAATAATG GTTGATCTTA AATCTGTATA CAAAATATCA CTGATATAAT GAACTCTCTC      4740

TCTCTAGACA AGATAAATTT TGCCTCCCCA TGAGATTTAT AGTGCTGAAG CCCTCTGTCA      4800

CTTGACACCC TTCTAGCCTT GTTGGAAGGG TTTTCAGGGA GATGGGGGCA CTATGGTTGC      4860

CCAAGACCAT AAACCCTCTT GTAGTCAGAC AGTATAGTGT AGCAGGGCAA TCTGTCTGAC      4920

ACCTAAATGG ACTTGAAATT GAAGCAGGAA GGTTGGGTTC TCCATGGATG GAACTCACCT      4980

GCCTGAACTG AGCAGGAATG TCAGTCTTCC ACTGCCCCTC CCTGCCATCT TCTGCTACTT      5040

AGCTTGGGAG TTGATGGTTG CAGAAGCCAC ACAGGGTTAA AGTAAATTCT GTCTTTGCCC      5100

ACCAGGGGAT CAAACCCCTG CTGATCTTGA TATCATATTT CTGTCATTTG CCAGTTGATG      5160

GAGCCAAGTT GACCTTTGGT TCTGGTGCTT CACCCAGTTT GGAACTTTAA TCTGTAACCC      5220

ATGGATCCAC AGATTTTCTT GGGAGCTTGA ATAGCCCTTC TTGGACAATG GGGTCTGGAA      5280

ATAGGGCTGT CTGCTTATGG AAATGCCATC TGTAGACCTT GAGAGTCAAC TGTACAGATG      5340

TTTGCAGGTG ACTCCTCGTG CC                                               5362

(2) INFORMATION FOR SEQ ID NO:4:

(i) SEQUENCE CHARACTERISTICS:
        (A) LENGTH: 1514 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Lys Asp Lys Gln Lys Arg Lys Lys Glu Arg Thr Trp Ala Glu Ala
    1               5                   10                  15

Ala Arg Leu Val Leu Glu Asn Tyr Ser Asp Ala Pro Met Thr Pro Lys
                20                  25                  30

Gln Ile Leu Gln Val Ile Glu Ala Glu Gly Leu Lys Glu Met Arg Ser
                    35                  40                  45

Gly Thr Ser Pro Leu Ala Cys Leu Asn Ala Met Leu His Ser Asn Ser
            50                  55                  60

Arg Gly Gly Glu Gly Leu Phe Tyr Lys Leu Pro Gly Arg Ile Ser Leu
    65                  70                  75                  80

Phe Thr Leu Lys Lys Asp Ala Val Gln Trp Ser Arg Asn Ala Ala Thr
                    85                  90                  95

Val Asp Gly Asp Glu Pro Glu Asp Ser Ala Asp Val Glu Ser Cys Gly
                100                 105                 110

Ser Asn Glu Ala Ser Thr Val Ser Gly Glu Asn Asp Val Ser Leu Asp
                115                 120                 125

Glu Thr Ser Ser Asn Ala Ser Cys Ser Thr Glu Ser Gln Ser Arg Pro
            130                 135                 140

Leu Ser Asn Pro Arg Asp Ser His Arg Ala Ser Ser Gln Ala Asn Lys
    145                 150                 155                 160
```

-continued

```
Gln Lys Lys Arg Thr Gly Val Met Leu Pro Arg Val Val Leu Thr Pro
                165                 170                 175
Leu Lys Val Asn Gly Ala His Val Glu Pro Ala Ser Gly Phe Ser Gly
                180                 185                 190
Arg His Ala Asp Gly Glu Ser Gly Ser Pro Ser Ser Ser Ser Ser Gly
                195                 200                 205
Ser Leu Ala Leu Gly Asn Ser Ala Ile Arg Gly Gln Ala Glu Val Thr
    210                 215                 220
Arg Asp Pro Ala Pro Leu Leu Arg Gly Phe Arg Lys Pro Ala Thr Gly
225                 230                 235                 240
Gln Met Lys Arg Asn Arg Gly Glu Glu Val Asp Phe Glu Thr Pro Gly
                245                 250                 255
Ser Ile Leu Val Asn Thr Asn Leu Arg Ala Leu Ile Asn Ser Arg Thr
                260                 265                 270
Phe His Ala Leu Pro Leu His Phe Gln Gln Gln Leu Leu Leu Leu Leu
                275                 280                 285
Pro Glu Val Asp Arg Gln Val Gly Thr Asp Gly Leu Leu Arg Leu Ser
                290                 295                 300
Gly Ser Ala Leu Asn Asn Glu Phe Phe Thr His Ala Ala Gln Ser Trp
305                 310                 315                 320
Arg Glu Arg Leu Ala Asp Gly Glu Phe Thr His Glu Met Gln Val Arg
                325                 330                 335
Leu Arg Gln Glu Met Glu Lys Glu Lys Lys Val Glu Gln Trp Lys Glu
                340                 345                 350
Lys Phe Phe Glu Asp Tyr Tyr Gly Gln Lys Leu Gly Leu Thr Lys Glu
                355                 360                 365
Glu Ser Leu Gln Gln Lys Glu Val Gln Glu Glu Ala Lys Val Lys Ser
                370                 375                 380
Gly Leu Cys Val Ser Gly Glu Ser Val Arg Pro Gln Arg Gly Pro Asn
385                 390                 395                 400
Thr Arg Gln Arg Asp Gly His Phe Lys Lys Arg Ser Arg Pro Asp Leu
                405                 410                 415
Arg Thr Arg Ser Arg Arg Asn Ile Tyr Lys Lys Gln Glu Pro Glu Gln
                420                 425                 430
Ala Gly Val Ala Lys Asp Ala Ser Ala Ala Pro Asp Val Ser Leu Ser
                435                 440                 445
Lys Asp Thr Lys Thr Asp Leu Ala Gly Val Asn Ser Thr Pro Gly Pro
450                 455                 460
Asp Val Ser Ser Ala Thr Ser Gly Gln Glu Gly Pro Lys Cys Pro Ser
465                 470                 475                 480
Glu Pro Val Ala Ser Gln Ile Gln Ala Glu Arg Asp Asn Leu Ala Cys
                485                 490                 495
Ala Ser Ala Ser Pro Asp Arg Ile Pro Thr Leu Pro Gln Asp Thr Val
                500                 505                 510
Asp Gln Glu Thr Lys Asp Gln Lys Arg Lys Ser Phe Glu Gln Glu Ala
                515                 520                 525
Ser Ala Ser Phe Pro Glu Lys Lys Pro Arg Leu Glu Asp Arg Gln Ser
                530                 535                 540
Phe Arg Asn Thr Ile Glu Ser Val His Thr Glu Lys Pro Gln Pro Thr
545                 550                 555                 560
Lys Glu Glu Pro Lys Val Pro Pro Ile Arg Ile Gln Leu Ser Arg Ile
                565                 570                 575
Lys Pro Pro Trp Val Ala Lys Gly Arg Pro Thr Tyr Gln Ile Cys Pro
                580                 585                 590
```

```
Arg Ile Val Pro Ile Thr Glu Ser Ser Cys Arg Gly Trp Thr Gly Ala
            595                 600                 605

Arg Thr Leu Ala Asp Ile Lys Ala Arg Ala Leu Gln Ala Arg Gly Ala
            610                 615                 620

Arg Gly Tyr His Cys Asn Arg Glu Thr Ala Thr Ala Ile Gly Gly
625                 630                 635                 640

Gly Gly Gly Pro Gly Gly Gly Ser Gly Ala Ile Asp Glu Gly Gly
                645                 650                 655

Gly Arg Asp Ser Ser Gly Asp Gly Ser Glu Ala Cys Gly His Pro
            660                 665                 670

Glu Pro Arg Gly Ala Pro Ser Thr Ser Gly Glu Ser Ala Ser Asp Leu
            675                 680                 685

Gln Arg Thr Gln Leu Leu Pro Pro Cys Pro Leu Asn Gly Glu His Thr
            690                 695                 700

Pro Ala Glu Ala Ala Met Pro Arg Ala Arg Glu Asp Ser Ala Ser
705                 710                 715                 720

Leu Arg Lys Glu Glu Ser Cys Leu Leu Lys Arg Val Pro Gly Val Leu
                725                 730                 735

Thr Ser Gly Leu Glu Asp Ala Ser Gln Pro Ile Ala Pro Thr Gly
            740                 745                 750

Asp Gln Pro Cys Gln Ala Leu Pro Pro Leu Ser Ser Gln Thr Pro Val
            755                 760                 765

Ala Glu Met Leu Thr Glu Gln Pro Lys Leu Leu Leu Asp Asp Arg Thr
770                 775                 780

Glu Cys Glu Ser Ser Arg Glu Asp Gln Gly Pro Thr Ile Pro Ser Glu
785                 790                 795                 800

Ser Ser Ser Gly Arg Phe Pro Leu Gly Asp Leu Leu Gly Gly Ser
                805                 810                 815

Asp Gln Ala Phe Asp Asn Met Lys Glu Pro Val Ser Met Thr Pro Thr
            820                 825                 830

Phe Ile Ser Glu Leu Ser Leu Ala Asn Tyr Leu Gln Asp Arg Pro Asp
            835                 840                 845

Asp Asp Gly Leu Gly Leu Gly Ala Thr Gly Leu Leu Ile Arg Glu Ser
            850                 855                 860

Ser Arg Gln Glu Ala Leu Thr Glu Ala Phe Ala Ser Gly Ser Pro Thr
865                 870                 875                 880

Ser Trp Val Pro Ile Leu Ser Asn Tyr Glu Val Ile Lys Thr Ser Asp
                885                 890                 895

Pro Glu Ser Arg Glu Asn Ile Pro Cys Pro Glu Pro Gln Asp Glu Lys
                900                 905                 910

Glu Trp Glu Arg Ala Val Pro Leu Ile Ala Ala Thr Glu Ser Val Pro
            915                 920                 925

Gln Pro Glu Ser Cys Ile Ser His Trp Thr Pro Pro Ala Ala Val
            930                 935                 940

Gly Ser Thr Gly Ser Asp Ser Glu Gln Val Asp Leu Glu Arg Leu Glu
945                 950                 955                 960

Met Asn Gly Ile Ser Glu Ala Pro Ser Pro His Ser Glu Ser Thr Asp
                965                 970                 975

Thr Ala Ser Asp Ser Glu Gly His Leu Ser Glu Asp Ser Ser Glu Val
            980                 985                 990

Asp Ala Ser Glu Val Thr Val Val Lys Gly Ser Leu Gly Gly Asp Glu
            995                 1000                1005

Lys Gln Asp Trp Asp Pro Ser Ala Ser Leu Ser Lys Val Asn Asn Asp
```

-continued

```
            1010                1015                1020
Leu Ser Val Leu Thr Arg Thr Gly Gly Val Ala Ala Ser Gln Ser Trp
1025                1030                1035                1040
Val Ser Arg Val Cys Ser Val Pro His Lys Ile Pro Asp Ser Leu Leu
                    1045                1050                1055
Leu Ser Ser Thr Glu Cys Gln Pro Arg Ser Val Cys Pro Leu Arg Pro
                    1060                1065                1070
Gly Ser Ser Val Glu Val Thr Asn Pro Leu Val Met His Leu Leu His
                    1075                1080                1085
Gly Asn Leu Pro Leu Glu Lys Val Leu Pro Pro Gly His Arg Ser Ser
        1090                1095                1100
Arg Leu Glu Ser Ser Gln Leu Pro Leu Arg Glu Gln Ser Gln Asp Arg
1105                1110                1115                1120
Gly Thr Leu Gln Gly Thr Gly Glu Asn Asn Arg Leu Ala Ala Arg Ile
                    1125                1130                1135
Asn Pro Gly Ser Ala Gln Thr Leu Lys Glu Ser Ile Leu Ala Gln Ser
                    1140                1145                1150
Tyr Gly Ala Ser Ala Gly Leu Val Arg Ala Met Ala Ser Lys Ala Pro
                    1155                1160                1165
Ala Met Ser Gln Lys Ile Ala Lys Met Val Thr Ser Leu Asp Ser Gln
1170                1175                1180
His Pro Glu Thr Glu Leu Thr Pro Ser Ser Gly Asn Leu Glu Glu Ile
1185                1190                1195                1200
Asp Ser Lys Glu His Leu Ser Ser Phe Leu Cys Glu Glu Gln Lys Glu
                    1205                1210                1215
Gly His Ser Leu Ser Gln Gly Ser Asp Pro Gly Ala Ala Pro Gly Gln
                    1220                1225                1230
Cys Leu Gly Asp His Thr Thr Ser Lys Val Pro Cys Phe Ser Ser Thr
        1235                1240                1245
Asn Val Ser Leu Ser Phe Gly Ser Glu Gln Thr Asp Gly Thr Leu Ser
        1250                1255                1260
Asp Gln Asn Asn Ala Gly Gly His Glu Lys Lys Leu Phe Gly Pro Gly
1265                1270                1275                1280
Asn Thr Val Thr Thr Leu Gln Cys Pro Arg Ser Glu Glu Gln Thr Pro
                    1285                1290                1295
Leu Pro Ala Glu Val Pro Pro Val Phe Pro Ser Arg Lys Ile Glu Pro
                    1300                1305                1310
Ser Lys Asn Ser Val Ser Gly Gly Val Gln Thr Thr Arg Glu Asn Arg
        1315                1320                1325
Met Pro Lys Pro Pro Pro Val Ser Ala Asp Ser Ile Lys Thr Glu Gln
        1330                1335                1340
Thr Phe Leu Arg Asp Pro Ile Lys Ala Asp Ala Glu Asn Arg Lys Ala
1345                1350                1355                1360
Ala Gly Tyr Ser Ser Leu Glu Leu Val Gly His Leu Gln Gly Met Pro
                    1365                1370                1375
Phe Val Val Asp Leu Pro Phe Trp Lys Leu Pro Arg Glu Pro Gly Lys
                    1380                1385                1390
Gly Phe Ser Gln Pro Leu Glu Pro Ser Ser Ile Pro Ser Gln Leu Asn
                    1395                1400                1405
Ile Lys Gln Ala Leu Tyr Gly Lys Leu Ser Lys Leu Gln Leu Ser Pro
        1410                1415                1420
Thr Ser Phe Asn Tyr Ser Ser Ser Ser Ala Thr Phe Pro Lys Gly Leu
1425                1430                1435                1440
```

```
Ala Gly Gly Val Val Gln Leu Ser His Lys Ala Ser Phe Gly Thr Gly
                1445                1450                1455

His Thr Ala Ser Leu Ser Leu Gln Met Phe Ala Asp Ser Ser Ala Val
            1460            1465                1470

Glu Ser Ile Ser Leu Gln Cys Ala Cys Ser Leu Lys Ala Met Ile Met
        1475            1480                1485

Cys Gln Gly Cys Gly Ala Phe Cys His Asp Asp Cys Ile Gly Pro Ser
    1490            1495            1500

Lys Leu Cys Val Leu Cys Leu Val Val Arg
1505            1510
```